(12) United States Patent
Kawai et al.

(10) Patent No.: US 6,849,757 B2
(45) Date of Patent: Feb. 1, 2005

(54) ANTIANGIOGENIC DRUG TO TREAT CANCER, ARTHRITIS AND RETINOPATHY

(75) Inventors: Megumi Kawai, Libertyville, IL (US); Jack Henkin, Highland Park, IL (US); George S. Sheppard, Wilmette, IL (US); Richard A. Craig, Racine, WI (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/616,628

(22) Filed: Jul. 10, 2003

(65) Prior Publication Data

US 2004/0110959 A1 Jun. 10, 2004

Related U.S. Application Data

(62) Division of application No. 09/316,856, filed on May 21, 1999, now Pat. No. 6,632,961.
(60) Provisional application No. 60/086,491, filed on May 22, 1998.

(51) Int. Cl.⁷ ............................................... C07C 69/76
(52) U.S. Cl. .................... 560/102; 560/41; 562/492; 564/169
(58) Field of Search ................... 560/102, 41; 562/492; 564/169

(56) References Cited

U.S. PATENT DOCUMENTS

| 4,147,802 A | 4/1979 | Cook et al. |
| 4,251,531 A | 2/1981 | Doria et al. |
| 4,540,689 A | 9/1985 | Muto |
| 5,446,062 A | 8/1995 | Dellaria |
| 5,453,533 A | 9/1995 | Luo |
| 5,703,199 A | 12/1997 | Henze |
| 5,741,926 A | 4/1998 | Bierer |
| 5,869,665 A | 2/1999 | Padia |

FOREIGN PATENT DOCUMENTS

| DE | 2654215 | 6/1977 |
| EP | 0183271 | 6/1986 |
| GB | 1498996 | 1/1978 |
| WO | 9119980 | 12/1991 |
| WO | 9404156 | 3/1994 |
| WO | 9723500 | 7/1997 |
| WO | 9741824 | 11/1997 |
| WO | 9961406 | 12/1999 |

OTHER PUBLICATIONS

Chem. Abst. 127:259879 (1997).*
Chem Abst 95:80296 (1980).*
Teno, et al., "Development of Selective Inhibitors Against Plasma Kallikrein", *Chemical and Pharmaceutical Bulletin*, vol. 39(11), pp. 2930–2936 (1991).
Goker, et al. "Synthesis and Antiaggregator Activity of Some New Derivatives of 4H–1–Benzopyran–4–one", *European Journal of Medicinal Chemisty*, vol. 30, pp. 561–567 (1995).
Kwon, et al., "Synthesis and Biological Activity of Cinnamaledeyhdes as Angiogenesis Inhibitors", *Bioorganic & Medicinal Chemistry Letters*, vol. 7(19), pp. 2473–2476 (1997).
Marui, et al., "Chemical Modifications of Fumagillin. II", *Chemical and Pharmaceutical Bulletin*, vol. 40(3), pp. 575–579 (1992).

* cited by examiner

*Primary Examiner*—Paul J. Killos
(74) *Attorney, Agent, or Firm*—Johanna M. Corbin

(57) ABSTRACT

Compounds having Formula I

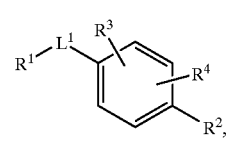

or pharmaceutically acceptable salts or prodrugs thereof, are useful for treating pathological states which arise from or are exacerbated by angiogenesis. The invention also relates to pharmaceutical compositions comprising these compounds and to methods of inhibiting angiogenesis in a mammal.

4 Claims, No Drawings

ANTIANGIOGENIC DRUG TO TREAT CANCER, ARTHRITIS AND RETINOPATHY

This application is a Divisional Application of U.S. patent application Ser. No. 09/316,856, filed May 21, 1999 now U.S. Pat. No. 6,632,961 present allowed, and claims the benefit of U.S. Provisional Patent Applications 60/086,491, filed May 22, 1998 incorporated herein by reference.

TECHNICAL FIELD

The present invention relates to compounds which are useful for treating pathological states which arise from or are exacerbated by angiogenesis, to pharmaceutical compositions comprising these compounds, and to methods of inhibiting angiogenesis in a mammal.

BACKGROUND OF THE INVENTION

Angiogenesis, the process by which new blood vessels are formed, is essential for normal body activities including reproduction, development and wound repair. Although the process is not completely understood, it is believed to involve a complex interplay of molecules which regulate the growth of endothelial cells (the primary cells of capillary blood vessels). Under normal conditions, these molecules appear to maintain the microvasculature in a quiescent state (i.e. one of no capillary growth) for prolonged periods which may last for as long as weeks or, in some cases, decades. When necessary (such as during wound repair), these same cells can undergo rapid proliferation and turnover within a 5 day period (Folkman, J. and Shing, Y., The Journal of Biological Chemistry, 267(16), 10931–10934, (1992) and Folkman, J. and Klagsbrun, M., Science, 235, 442–447 (1987).

Although angiogenesis is a highly regulated process under normal conditions, many diseases (characterized as angiogenic diseases) are driven by persistent unregulated angiogenesis. Otherwise stated, unregulated angiogenesis may either cause a particular disease directly or exacerbate an existing pathological condition. For example, ocular neovascularization has been implicated as the most common cause of blindness and dominates approximately twenty eye diseases. In certain existing conditions, such as arthritis, newly formed capillary blood vessels invade the joints and destroy cartilage. In diabetes, new capillaries formed in the retina invade the vitreous, bleed, and cause blindness. Growth and metastasis of solid tumors are also dependent on angiogenesis (Folkman, J., Cancer Research, 46, 467–473 (1986), Folkman, J., Journal of the National Cancer Institute, 82, 4–6 (1989). It has been shown, for example, that tumors which enlarge to greater than 2 mm must obtain their own blood supply and do so by inducing the growth of new capillary blood vessels. Once these new blood vessels become embedded in the tumor, they provide a means for tumor cells to enter the circulation and metastasize to distant sites such as liver, lung or bone (Weidner, N., et al., The New England Journal of Medicine, 324(1), 1–8 (1991).

Several angiogenesis inhibitors are currently under development for use in treating angiogenic diseases (Gasparini, G. and Harris, A. L., J. Clin. Oncol., 13(3): 765–782, (1995), but there are disadvantages associated with these compounds. Suramin, for example, is a potent angiogenesis inhibitor but causes severe systemic toxicity in humans at doses required for antitumor activity. Compounds such as retinoids, interferons and antiestrogens are relatively safe for human use but have weak antiangiogenic effects. Irsogladine, an anti-tumor drug with low toxicity, has only weak anti-angiogenic effects. Thus there is still a need for compounds useful in treating angiogenic diseases in mammals.

SUMMARY OF THE INVENTION

In one embodiment of the present invention are disclosed compounds represented by Formula I

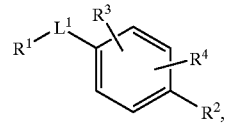

or a pharmaceutically acceptable salt or prodrug thereof, where $L^1$ is selected from
(1) a covalent bond,
(2) —C(O)NR$^5$(CH$_2$)$_m$—, where m is an integer from 0 to 4, and
   $R^5$ is selected from
   (a) hydrogen
   and
   (b) alkyl,
and
(3) —N(R$^5$)C(O)(CH$_2$)$_m$,
where (2) and (3) are drawn with their left ends attached to $R^1$;
$R^1$ is selected from
(1) alkyl,
(2) alkyl substituted with 1, 2, or 3 substituents selected from
   (a) —NO$_2$
   (b) —NR$^6$R$^7$ where $R^6$ and $R^7$ are independently selected from
      (i) hydrogen,
      (ii) alkyl,
      (iii) arylalkyl,
      (iv) an amino protecting group,
      (v) alkanoyl, where the alkanoyl can be optionally substituted with —OR$^9$,
      (vi) (aryl)oyl,
      (vii) alkoxycarbonyl,
      and
      (viii) (heteroaryl)oyl,
   and
   (c) alkoxycarbonyl,
(3) aryl substituted with 1, 2, 3, 4, or 5 substituents independently selected from
   (a) —NR$^6$R$^7$,
   (b) alkyl,
   and
   (c) alkyl substituted with 1, 2, or 3 substituents selected from —NR$^6$R$^7$,
(4) —NR$^6$R$^7$,
and
(5) —OR$^9$;
$R^2$ and $R^3$ are selected from
(1) hydrogen
(2) —(CH$_2$)$_n$C(O)R$^8$ where n is an integer from 0 to 4, and
   $R^8$ is selected from
   (a) —OR$^9$ where $R^9$ is selected from
      (i) hydrogen, (ii) alkyl,
and
(iii) alkyl substituted with 1 or 2 substituents selected from the group consisting of aryl
and
(b) —$NR^5R^{10}$ where $R^5$ is defined previously, and $R^{10}$ is selected from
  (i) hydrogen,
  (ii) alkyl,
  (iii) alkyl substituted with 1, 2, or 3 substituents independently selected from
    (1') —$CO_2R^9$
    and
    (2') —$C(O)NR^6R^7$
  (iv) aryl,
  and
  (v) arylalkyl,
  where (iv) and (v) can be optionally substituted with 1, 2, 3, 4, or 5 substituents
    independently selected from
    (1') alkyl,
    (2') alkanoyl,
    (3') —$OR^9$,
    (4') —$CO_2R^9$,
    (5') alkanoyloxy,
    (6') carboxaldehyde,
    (7') cycloalkyl,
    (8') cycloalkenyl,
    (9') halo,
    (10') nitro,
    (11') perfluoroalkyl,
    (12') perfluoroalkoxy,
    (13') —$NR^6R^7$,
    (14') —$SO_2NR^6R^7$,
    (15') —$C(O)NR^6R^7$,
    (16') aryloxy,
    and
    (17') aryl,
and
(3) aryl, wherein the aryl is optionally substituted with 1, 2, or 3 substituents independently
  selected from
  (a) —$NR^6R^7$
  and
  (b) —$CO_2R^9$,
provided that at least one of $R^2$ and $R^3$ is other than hydrogen;
$R^4$ is selected from
(1) hydrogen,
(2) alkyl,
(3) cycloalkyl,
(4) —$CO_2R^5$,
(5) aryl,
and
(6) aryl substituted with at least one of W, X, Y, or Z where W, X, Y, and Z are independently selected from
  (a) alkyl,
  (b) alkanoyl,
  (c) —$OR^9$,
  (d) —$CO_2R^9$,
  (e) alkanoyloxy,
  (f) carboxaldehyde,
  (g) cycloalkyl,
  (h) cycloalkenyl,
  (i) halo,
  (j) nitro,
  (k) perfluoroalkyl,
  (l) perfluoroalkoxy,
  (m) —$NR^6R^7$,
  (n) —$SO_2NR^6R^7$,
  (o) —$C(O)NR^6R^7$,
  (p) aryloxy,
  and
  (q) aryl.

In another embodiment of the invention are disclosed methods of treating diseases comprising administering an effective amount of a compound having Formula I.

In yet another embodiment of the invention are disclosed pharmaceutical compositions containing compounds of Formula I.

Compounds of this invention include, but are not limited to,

N-[4-[N-(acetylglycyl)amino]benzoyl]-L-aspartic acid,

4-[[4-(aminomethyl)benzoyl]amino]-2-phenylbenzoic acid,

N-[4-[(7-amino-1-oxoheptyl)amino]benzoyl]-L-aspartic acid, (S)-methyl 3-[[6-amino-2-[[(1,1-dimethylethoxy)carbonyl]amino]-1-oxohexyl]amino]-4-(1,1-dimethylethyl)benzoate, (S)-methyl 3-[[2-(acetylamino)-6-amino-1-oxohexyl]aamino]4-(1,1-dimethylethyl)benzoate, (S)-3-[[2-(acetylamino)-6-amino-1-oxohexyl)amino]-4-(1,1-dimethylethyl)benzoic acid, (S)-methyl 4-[[2-[[(1,1-dimethylethoxy)carbonyl]amino]-6 [(phenylmethoxy)carbonyl]amino]-1-oxohexyl]amino]-2-[3-(phenylmethoxy)-phenyl]benzoate, (S)-1,1-dimethylethyl 4-[[2-[[(1,1-dimethylethoxy)carbonyl]amino]-6-[(phenylmethoxy)carbonyl]amino]-1-oxohexyl]amino]-2-[3-(phenylmethoxy)phenyl]benzoate, (R)-methyl 4-[[6-amino-2-[[(1,1-dimethylethoxy)carbonyl]amino]-1-oxohexyl]amino]-2-(3-hydroxyphenyl)benzoate, (R)-methyl 4-[[6-amino-2-[[(1,1-dimethylethoxy)carbonyl]amino]-1-oxohexyl]amino]-2-(2-hydroxyphenyl)benzoate, (S)-methyl 4-[[2-amino-6-[[(phenylmethoxy)carbonyl]amino]-1-oxohexyl]amino]-2-[(3-(phenylmethoxy)phenyl]benzoate, (S)-methyl 4-[[2-(acetylamino)-6-[[(phenylmethoxy)carbonyl]amino]-1-oxohexyl]amino]-2-[(3-(phenylmethoxy)phenyl] benzoate, (S)-1,1-dimethylethyl 4-[[6-amino-2-[[(1,1-dimethylethoxy)carbonyl]amino]-1-oxohexyl]amino]-2-(3-hydroxyphenyl)benzoate, (S)-methyl 4-[[2-(acetylamino)-6-amino-1-oxohexyl]amino]-2-(3-hydroxyphenyl)benzoate, (S)-4-[[2-(acetylamino)-6-amino-1-oxohexyl)amino]-2-(3-hydroxyphenyl)benzoic acid, (S)-N-[4-[[2-(acetylamino)-6-amino-1-oxohexyl]amino)-2-(3-hydroxyphenyl)benzoyl]-L-α-asparagine, (S)-N-[4-[[2-(acetylamino)-6-amino-1-oxohexyl]amino]-2-phenylbenzoyl]-L-α-asparagine, (S)-N-[4-[[2-(acetylamino)-6-amino-1-oxohexyl]amino)benzoyl)-L-α-asparagine, N-[(4-aminophenyl)acetyl]-L-aspartic acid, bis(1,1-dimethylethyl) ester, (S)-N-[[4-[[2-amino-6-[[(phenylmethoxy)carbonyl]amino]-1-oxohexyl]amino]phenyl]acetyl]-L-aspartic acid, (S)-N-[[4-[[2-(acetylamino)-6-[[(phenylmethoxy)carbonyl]amino]-1-oxohexyl]amino]phenyl]acetyl]-L-aspartic acid, N-[2-[[4-[2-(acetylamino)-6-amino-1-oxohexyl]amino]phenyl]-1-oxoethyl]-L-aspartic acid, (S)-N-[[4-[[6-amino-2-[[(1,1-dimethylethoxy)carbonyl]amino]-1-oxohexyl]amino]phenyl]acetyl]-L-aspartic acid, bis(1,1-diemthylethyl) ester, (S)-N-[[4-((2,6-diamino-1-oxohexyl)amino]phenyl]acetyl]-L-aspartic acid, (S)-ethyl 4-[[6-amino-2-[[(1,1-dimethylethoxy)carbonyl]amino]-1-oxohexyl]amino]benzeneacetate, (S)-4-[[6-amino-2-[[(1,1-dimethylethoxy)carbonyl]amino]-1-oxohexyl]amino]benzeneacetic acid, methyl 5-(((2S)-6-amino-2-((tert-butoxycarbonyl)amino)hexanoyl)amino)-4'-hydroxy(1,1'-biphenyl)-2-carboxylate, (3S)-3-(((5-(((2S)-2-(acetylamino)-6-aminohexanoyl)amino)-4'-hydroxy(1,1'-biphenyl)-2-yl)carbonyl)amino)-4-amino-4-oxobutanoic acid, methyl 3-(((2S)-6-amino-2-((tert-butoxycarbonyl)amino)hexanoyl)amino)-4-cyclohexylbenzoate, tert-butyl (3S)-3-(((5-(((2S)-2-(acetylamino)-6-aminohexanoyl)amino)-3'-hydroxy(1,1'-biphenyl)-2-yl)carbonyl)amino)-4-amino-4-oxobutanoate, 5-(((2S)-6-amino-2-((tert-butoxycarbonyl)amino)hexanoyl)amino)-3'-hydroxy(1,1'-biphenyl)-2-carboxylic acid, methyl 5-(((2S)-2,6-diaminohexanoyl)amino)-3'-hydroxy(1,1'-biphenyl)-2-carboxylate, 5-(((2S)-6-amino-2-((2,2-dimethylpropanoyl)amino)hexanoyl)amino)-3'-hydroxy(1,1'-biphenyl)-2-carboxylic acid, methyl 5-(((2S)-6-amino-2-((2,2-dimethylpropanoyl)amino)hexanoyl)amino)-3'-hydroxy(1,1'-biphenyl)-2-carboxylate, 5-(((2S)-6-amino-2-(benzoylamino)hexanoyl)amino)-3'-hydroxy(1,1'-biphenyl)-2-carboxylic acid, 5-(((2S)-6-amino-2-((methoxycarbonyl)amino)hexanoyl)amino)-3'-hydroxy(1,1'-biphenyl)-2-carboxylic acid, (4S)-4-((4-(((2S)-2-(acetylamino)-6-aminohexanoyl)amino)benzoyl)amino)-5-(methylamino)-5-oxopentanoic acid, 4-(((2S)-6-amino-2-((tert-butoxycarbonyl)amino)hexanoyl)amino)benzoic acid, (3S)-3-((4-(((2S)-2-(acetylamino)-6-aminohexanoyl)amino)benzoyl)amino)-4-amino-4-oxobutanoic acid, methyl 4-(((2S)-6-amino-2-((tert-butoxycarbonyl)amino)hexanoyl)amino)benzoate, methyl 5-(((2S)-2-((tert-butoxycarbonyl)amino)hexanoyl)amino)-3'-hydroxy(1,1'-biphenyl)-2-carboxylate, 4-(((2S)-6amino-2-((tert-butoxycarbonyl)amino)hexanoyl)amino)-2-chlorobenzoic acid, 5-(((2S)-2-(acetylamino)-6-aminohexanoyl)amino)-N-(2-hydroxyphenyl)(1,1'-biphenyl)-2-carboxamide, 5-(((2S)-2-(acetylamino)-6-aminohexanoyl)amino)-N-(3-hydroxyphenyl)(1,1'-biphenyl)-2-carboxamide, 5-(((2S)-2-(acetylamino)-6-aminohexanoyl)amino)-N-(4-hydroxyphenyl)(1,1'-biphenyl)-2-carboxamide, methyl 5-(((2S)-6-amino-2-(((benzyloxy)carbonyl)amino)hexanoyl)amino)(1,1'-biphenyl)-2-carboxylate, 5-(((2S)-2-((tert-butoxycarbonyl)amino)-6-((3-pyridinylcarbonyl)amino)hexanoyl)amino)-3'-hydroxy(1,1'-biphenyl)-2-carboxylic acid, 5-(((2S)-2-(acetylamino)-6-aminohexanoyl)amino)(1,1'-biphenyl)-2-carboxylic acid, 5-((6-aminohexanoyl)amino)-3'-hydroxy(1,1'-biphenyl)-2-carboxylic acid, 5-(((2S)-2-((tert-butoxycarbonyl)amino)hexanoyl)amino)-3'-hydroxy(1,1'-biphenyl)-2-carboxylic acid, 5-(((2S)-5-amino-2-((tert-butoxycarbonyl)amino)pentanoyl)amino)-3'-hydroxy(1,1'-biphenyl)-2-carboxylic acid, (2S)-2-(((5-(((2S)-2-(acetylamino)-6-aminohexanoyl)amino)(1,1'-biphenyl)-2-yl)carbonyl)amino)butanedioic acid, 5-(((2S)-2-((tert-butoxycarbonyl)amino)-6-(methylamino)hexanoyl)amino)-3'-hydroxy(1,1'-biphenyl)-2-carboxylic acid, 5-(((2S)-2-(acetylamino)-6-aminohexanoyl)amino)-N-(4-(aminosulfonyl)phenethyl)(1,1'-biphenyl)-2-carboxamide, ethyl 2-(((5-(((2S)-2-(acetylamino)-6-aminohexanoyl)amino)(1,1'-biphenyl)-2-yl)carbonyl)amino)benzoate, ethyl 3-(((5-(((2S)-2-(acetylamino)-6-aminohexanoyl)amino)(1,1'-biphenyl)-2-yl)carbonyl)amino)benzoate, ethyl 4-(((5-(((2S)-2-(acetylamino)-6-aminohexanoyl)amino)(1,1'-biphenyl)-2-yl)carbonyl)amino)benzoate, 5-(((2S)-2-(acetylamino)-6-aminohexanoyl)amino)-N-(4-(aminosulfonyl)benzyl)(1,1'-biphenyl)-2-carboxamide, 2-(((5-(((2S)-2-(acetylamino)-6-(((benzyloxy)carbonyl)amino)-hexanoyl)amino)(1,1'-biphenyl)-2-yl)carbonyl)amino)benzoic acid, 3-(((5-(((2S)-2-(acetylamino)-6-(((benzyloxy)carbonyl)amino)-hexanoyl)amino(1,1'-biphenyl)-2-yl)carbonyl)amino)benzoic acid, 4-(((5-(((2S)-2-(acetylamino)-6-(((benzyloxy)carbonyl)amino)-hexanoyl)amino)(1,1'-biphenyl)-2-yl)carbonyl)amino)benzoic acid, 2-(((5-(((2S)-2-(acetylamino)-6-aminohexanoyl)amino)(1,1'-biphenyl)-2-yl)carbonyl)amino)benzoic acid, 3-(((5-(((2S)-2-(acetylamino)-6-aminohexanoyl)amino)(1,1'-biphenyl)-2-yl)carbonyl)amino)benzoic acid, and 4-(((5-(((2S)-2-(acetylamino)-6-aminohexanoyl)amino)(1,1'-biphenyl)-2-yl)carbonyl)amino)benzoic acid.

DETAILED DESCRIPTION OF THE INVENTION

Definition of Terms

The term "alkanoyl," as used herein, refers to an alkyl group attached to the parent molecular group through a carbonyl. The alkanoyl groups of this invention can be optionally substituted.

The term "alkoxy," as used herein, refers to an alkyl group attached to the parent molecular group through an oxygen atom. The alkanoyl groups of this invention can be optionally substituted.

The term "alkoxycarbonyl," as used herein, refers to an alkoxy group attached to the parent molecular group through a carbonyl. The alkoxycarbonyl groups of this invention can be optionally substituted.

The term "alkanoyloxy," as used herein, refers to an alkanoyl group attached to the parent molecular group through an oxygen atom. The alkanoyloxy groups of this invention can be optionally substituted.

The term "alkyl," as used herein, refers to a monovalent straight or branched chain group of one to twelve carbons derived from a saturated hydrocarbon by the removal of a hydrogen atom. The alkyl groups of this invention can be optionally substituted.

The term "amino," as used herein, refers to —NH$_2$.

The term "aryl," as used herein, refers to a mono- or bicyclic carbocyclic ring system having one or two aromatic rings. The aryl group can also be fused to a cyclohexane, cyclohexene, cyclopentane or cyclopentene ring. The aryl groups of this invention can be optionally substituted.

The term "aryloxy" as used herein, refers to an aryl group attached to the parent molecular group through an oxygen atom. The aryloxy groups of this invention can be optionally substituted.

The term "arylalkyl," as used herein, refers to an aryl group attached to the parent molecular group through an alkyl group. The arylalkyl groups of this invention can be optionally substituted.

The term "carbonyl," as used herein, refers to —C(O)—.

The term "carboxaldehyde," as used herein, refers to —CHO.

The term "cycloalkyl," as used herein, refers to a monovalent group of four to twelve carbons derived from a cyclic or bicyclic hydrocarbon having at least one carbon-carbon double bond. The cycloalkenyl groups of this invention can be optionally substituted.

The term "cycloalkyl," as used herein, refers to a monovalent group of three to twelve carbons derived from a saturated cyclic or bicyclic hydrocarbon by the removal of a hydrogen atom. The cycloalkyl groups of this invention can be optionally substituted.

The term "halo," as used herein, refers to —F, —Br, —Cl, or —I.

The term "heteroaryl," as used herein, refers to an five- or six-membered aromatic ring containing at least one oxygen, nitrogen, or sulfur atom. The sulfur atoms can be optionally oxidized, and the nitrogen atoms can be optionally oxidized or quaternized. Heterocycles of the invention are exemplified by those derived from furan, thiophene, pyrrole, imidazole, oxazole, thiazole, isoxazole, isothiazole, 1,2,3-oxadiazole, 1,2,3-triazole, 1,3,4-thiadiazole, pyridine, pyridazine, pyrimidine, pyrazine, and 1,3,5-triazine. The heteroaryl groups of this invention can be optionally substituted.

The term "(heteroaryl)oyl," as used herein, refers to a heteroaryl group attached to the parent molecular group through a carbonyl.

The term "N-protected amino" or "amino protecting group," as used herein, refers to groups intended to protect an amino group against undesirable reactions during synthetic procedures. Commonly used N-protecting groups are disclosed in Greene, T. W., & Wuts, P. G. M. (1991). *Protectective Groups In Organic Synthesis* (2nd ed.). New York: John Wiley & Sons. Preferred N-protecting groups are formyl, acetyl, benzoyl, pivaloyl, t-butylacetyl, phenylsulfonyl, benzyl, t-butyloxycarbonyl (Boc), and benzyloxycarbonyl (Cbz).

The term "nitro," as used herein, refers to —NO$_2$.

The term "perfluoroalkoxy," as used herein, refers to a perfluoroalkyl group attached to the parent molecular group through an oxygen atom.

The term "perfluoroalkyl," as used herein, refers to an alkyl group wherein all of the hydrogen atoms have been replaced with fluoride atoms.

The term "pharmaceutically acceptable prodrugs," as used herein, presents those prodrugs of the compounds of the present invention which are, within the scope of sound medical judgement, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as used herein, represents those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 1977, 66:1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The term "prodrug," as used herein, represents compounds which are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

Compounds of the present invention can exist as stereoisomers where asymmetric or chiral centers are present. These compounds are designated by the symbols "R" or "S," depending on the configuration of substitiuents around the chiral carbon atom. The present invention contemplates various stereoisomers and mixtures thereof. Stereoisomers include enantiomers and diastereomers, and equal mixtures of enantiomers are designated (±). Individual stereoisomers of compounds of the present invention can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of enantiomers on chiral chromatographic columns.

Determination of Biological Activity

Endothelial Cell Migration Assay

The endothelial cell migration assay was performed essentially as described by Polverini, P. J. et al., Methods Enzymol, 198: 440–450 (1991). Briefly, Human Microvascular Endothelial Cells (HMVEC) were starved overnight in DMEM containing 0.1% bovine serum albumin (BSA). Cells were then harvested with trypsin and resuspended in DMEM with 0.1% BSA at a concentration of 1.5×10$^6$ cells/mL. Cells were added to the bottom of a 48-well modified Boyden chamber (Nucleopore Corporation, Cabin John, Md.). The chamber was assembled and inverted, and cells were allowed to attach for 2 hours at 37° C. to polycarbonate chemotaxis membranes (5 μm pore size) that had been soaked in 0.1% gelatin overnight and dried. The chamber was then reinverted and basic fibroblast growth factor (bFGF) and test substances were added to the wells of the upper chamber (to a total volume of 50 μL); the apparatus was then incubated for 4 hours at 37° C. Membranes were recovered, fixed and stained (DiffQuick, Fisher Scientific, Pittsburgh, Pa.) and the number of cells that had migrated to the upper chamber per 10 high power fields were counted. Background migration to DMEM+0.1% BSA was subtracted and the data reported as the number of cells migrated per 10 high power fields (400×) or when results from multiple experiments were combined, as the percent inhibition of migration compared to a positive control. The results are shown in Table 1.

TABLE 1

Inhibitory Potencies Against Human Microvascular Endothelial Cell Migration of Representative Compounds

| Example | % inhibition at 200 nM test compound |
|---------|--------------------------------------|
| 9       | >95                                  |
| 10      | 80                                   |
| 12      | 29                                   |
| 14      | 60                                   |
| 15      | 64                                   |
| 16      | 86                                   |
| 17      | >95                                  |
| 18      | 90                                   |
| 19      | 32                                   |
| 20      | 34                                   |
| 25      | 38                                   |
| 27      | 28                                   |
| 28      | 59                                   |
| 31      | >95                                  |

The compounds of the invention, including but not limited to those specified in the examples, possess antiangiogenic activity. As angiogenesis inhibitors, such compounds are useful in the treatment of both primary and metastatic solid tumors and carcinomas of the breast; colon; rectum; lung; oropharynx; hypopharynx; esophagus; stomach; pancreas; liver; gallbladder; bile duct; small intestine; urinary tract including kidney, bladder and urothelium; female genital tract including cervix, uterus, ovaries, choriocarcinoma and gestational trophoblastic disease; male genital tract including prostate, seminal vesicles, testes and germ cell tumors; endocrine glands including thyroid, adrenal, and pituitary; skin including hemangiomas, melanomas, sarcomas arising from bone or soft tissues and Kaposi's sarcoma; tumors of the brain, nerves, eyes, and meninges including astrocytomas, gliomas, glioblastomas, retinoblastomas, neuromas, neuroblastomas, Schwannomas and meningiomas; solid tumors arising from hematopoietic malignancies such as leukemias and including chloromas, plasmacytomas, plaques and tumors of mycosis fungoides and cutaneous T-cell lymphoma/leukemia; lymphomas including both Hodgkin's and non-Hodgkin's lymphomas; prophylaxis of auto immune diseases including rheumatoid, immune and degenerative arthritis; ocular diseases including diabetic retinopathy, retinopathy of prematurity, corneal graft rejection, retrolental fibroplasia, neovascular glaucoma, rubeosis, retinal neovascularization due to macular degeneration and hypoxia; abnormal neovascularization conditions of the eye; skin diseases including psoriasis; blood vessel diseases including hemagiomas and capillary proliferation within atherosclerotic plaques; Osler-Webber Syndrome; myocardial angiogenesis; plaque neovascularization; telangiectasia; hemophiliac joints; angiofibroma; wound granulation; diseases characterized by excessive or abnormal stimulation of endothelial cells including intestinal adhesions, Crohn's disease, atherosclerosis, scleroderma and hypertrophic scars (i.e. keloids) and diseases which have angiogenesis as a pathologic consequence including cat scratch disease (*Rochele minalia quintosa*) and ulcers (*Helicobacter pylori*). Another use is as a birth control agent which inhibits ovulation and establishment of the placenta.

The compounds of the present invention may also be useful for the prevention of metastases from the tumors described above either when used alone or in combination with radiotherapy and/or other chemotherapeutic treatments conventionally administered to patients for treating cancer. For example, when used in the treatment of solid tumors, compounds of the present invention may be administered with chemotherapeutic agents such as alpha inteferon, COMP (cyclophosphamide, vincristine, methotrexate and prednisone), etoposide, mBACOD (methortrexate, bleomycin, doxorubicin, cyclophosphamide, vincristine and dexamethasone), PRO-MACE/MOPP (prednisone, methotrexate (w/leucovin rescue), doxorubicin; cyclophosphamide, taxol, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and the like. Other chemotherapeutic agents include alkylating agents such as nitrogen mustards including mechloethamine, melphan, chlorambucil, cyclophosphamide and ifosfamide; nitrosoureas including carmustine, lomustine, semustine and streptozocin; alkyl sulfonates including busulfan; triazines including dacarbazine; etheyenimines including thiotepa and hexamethylmelamine; folic acid analogs including methotrexate; pyrimidine analogues including 5-fluorouracil, cytosine arabinoside; purine analogs including 6-mercaptopurine and 6-thioguanine; antitumor antibiotics including actinomycin D; the anthracyclines including doxorubicin, bleomycin, mitomycin C and methramycin; hormones and hormone antagonists including tamoxifen and cortiosteroids and miscellaneous agents including cisplatin and brequinar.

The compounds of the present invention may be used in the form of pharmaceutically acceptable salts derived from inorganic or organic acids. By "pharmaceutically acceptable salt" is meant those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge, et al. describe pharmaceutically acceptable salts in detail in J. Pharmaceutical Sciences, 1977, 66: 1 et seq. The salts may be prepared in situ during the final isolation and purification of the compounds of the invention or separately by reacting a free base function with a suitable acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Preferred salts of the compounds of the invention include phosphate, tris and acetate.

Compounds of this invention may be combined with pharmaceutically acceptable sustained-release matrices, such as biodegradable polymers, to form therapeutic pocompositions. A sustained-release matrix, as used herein, is a matrix made of materials, usually polymers, which are degradable by enzymatic or acid-base hydrolysis or by dissolution. Once inserted into the body, the matrix is acted upon by enzymes and body fluids. A sustained-release matrix is desirably chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

Compounds of this invention or combinations thereof may be combined with pharmaceutically acceptable excipients or carriers to form therapeutic compositions. A pharmaceutically acceptable carrier or excipient refers to a non-toxic solid, semi-solid or liquid filler, diluent, encapsulating material or formulation auxiliary of any type. The compositions may be administered parenterally, sublingually, intracisternally, intravaginally, intraperitoneally, rectally, bucally or topically (as by powder, ointment, drops, transdermal patch or iontophoresis device).

The term "parenteral," as used herein, refers to modes of administration which include intravenous, intramuscular, intraperitoneal, intrasternal, subcutaneous and intraarticular injection and infusion. Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents and dispersing agents. Prevention of the action of microorganisms may be ensured by the inclusion of various antibacterial and antifungal agents such as paraben, chlorobutanol, phenol, sorbic acid and the like. It may also be desirable to include isotonic agents such as sugars, sodium chloride and the like. Prolonged absorption of the injectable pharmaceutical form may be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations may be sterilized, for example, by filtration through a bacterial-retaining filter or by incorporating sterilizing agents in the form of sterile solid compositions which can be dissolved or dispersed in sterile water or other sterile injectable media just prior to use.

Topical administration includes administration to the skin, mucosa and surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers. For topical administration to the eye, a compound of the invention is delivered in a pharmaceutically acceptable ophthalmic vehicle such that the compound is maintained in contact with the ocular surface for a sufficient time period to allow the compound to penetrate the corneal and internal regions of the eye, as, for example, the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material. Alternatively, a compound of the invention may be injected directly into the vitreous and aqueous humor.

The composition may be pressurized and contain a compressed gas such as nitrogen or a liquified gas propellant. The liquified propellant medium and indeed the total composition is preferably such that the active ingredient does not dissolve therein to any substantial extent. The pressurized composition may also contain a surface active agent such as a liquid or solid non-ionic surface active agent or may be a solid anionic surface active agent. It is preferred to use the solid anionic surface active agent in the form of a sodium salt.

Compositions for rectal or vaginal administration are preferably suppositories which may be prepared by mixing the compounds of this invention with suitable non-irritating excipients or carriers such as cocoa butter, polyethylene glycol or a suppository wax which are solids at room temperature but liquids at body temperature and therefore melt in the rectum or vaginal cavity and release the active compound.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form may contain, in addition to a compound of the present invention, stabilizers, preservatives, excipients and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq., which is hereby incorporated herein by reference.

When used in the above or other treatments, a therapeutically effective amount of one of the compounds of the present invention may be employed in pure form or, where such forms exist, in pharmaceutically acceptable salt form and with or without a pharmaceutically acceptable excipient. A "therapeutically effective amount" of the compound of the invention means a sufficient amount of the compound to treat an angiogenic disease (for example, to limit tumor growth or to slow or block tumor metastasis) at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of the compound at levels lower than those required to achieve the desired therapeutic effect and to gradually increase the dosage until the desired effect is achieved. Total daily dose of compounds of this invention to be administered locally or systemically to a human or other mammal host in single or divided doses may be in amounts, for example, from 0.01 to 200 mg/kg body weight daily and more usually 1 to 300 mg/kg body weight. If desired, the effective daily dose may be divided into multiple doses for purposes of administration. Consequently, single dose compositions may contain such amounts or submultiples thereof to make up the daily dose.

It will be understood that agents which can be combined with the compound of the present invention for the inhibition, treatment or prophylaxis of angiogenic diseases are not limited to those listed above, but include, in principle, any agents useful for the treatment or prophylaxis of angiogenic diseases.

Preparation of Compounds of the Invention

Abbreviations

Abbreviations which have been used in the descriptions of the scheme and the examples that follow are: NMM for 4-methylmorpholine; EDCI for 1-ethyl-3-[3-(dimethylamino)propyl]-carbodiimide hydrochloride; HOBT for hydroxybenztriazole; TFA for trifluoroacetic acid; THF for tetrahydrofuran; DMF for dimethylformamide.

Synthetic Methods

The compounds and processes of the present invention will be better understood in connection with the following synthetic schemes which illustrate the methods by which the compounds of the invention may be prepared. The compounds of this invention may be prepared by a variety of synthetic routes. A representative procedure is outlined in Scheme 1 where $L^1$, $R^1$, $R^2$, $R^3$ and $R^4$ are defined previously unless indicated otherwise. Depending on the nature of $L^1$, $R^1$, $R^2$, $R^3$, and $R^4$, protection and subsequent deprotection of other reactive groups can be required to successfully complete the described synthetic sequences. Commonly used protecting groups are disclosed in Greene, "Protective Groups In Organic Synthesis," (John Wiley & Sons, New York (1981)), which is incorporated herein by reference. It will be readily apparent to one of ordinary skill in the art reviewing the synthetic route depicted below that other compounds within Formula I can be synthesized by the substitution of appropriate reactants and agents in the synthesis shown below.

Scheme 1

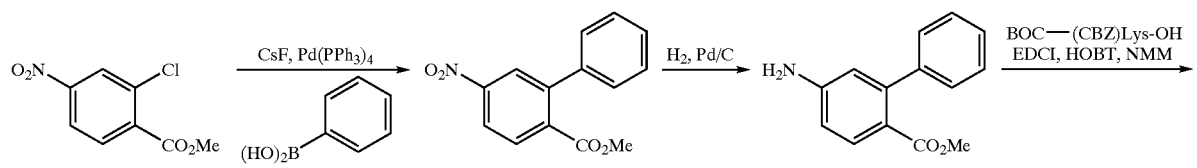

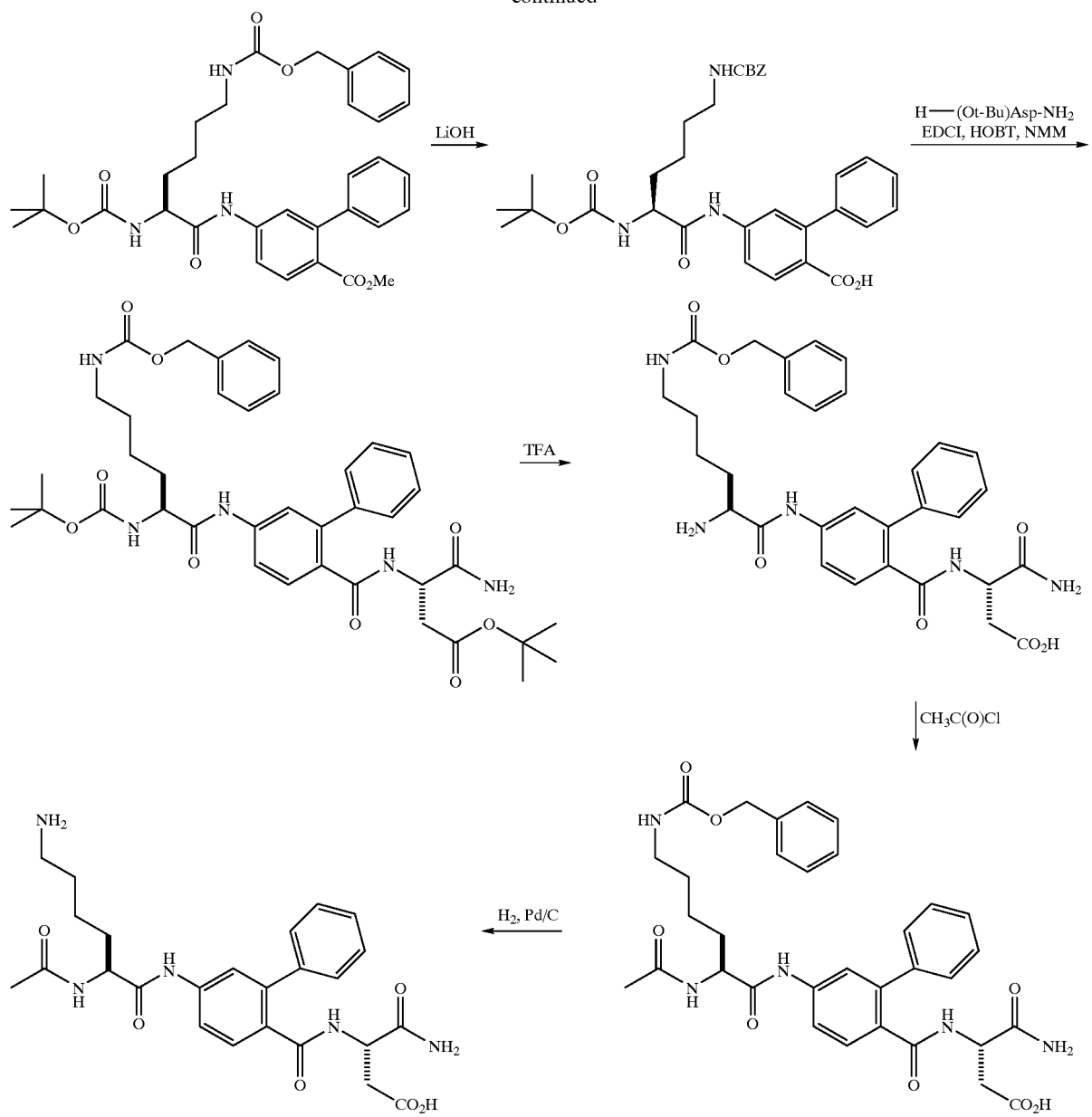

As exemplified in Scheme 1, a biaryl coupling was accomplished with methyl-2-chloro-4-nitrobenzoate and a boronic acid in the presence of a palladium catalyst such as tetrakis(triphenylphosphine)palladium(0). The nitro moiety was reduced to an amine with hydrogen gas in the presence of 10% palladium on carbon. Lysine was then coupled to the aniline derivative with EDCI, HOBt and a base preferably NMM. The ester was saponified with lithium hydroxide and aspartic acid coupled to the benzoic acid derivative with EDCI, HOBT and a base preferably NMM. The N-Boc group and t-butyl esters were removed with TFA to give the amino acid. The free amine was acetylated with acetyl chloride, and the CBZ group was removed under hydrogen gas in the presence of 10% palladium on carbon.

The compounds and processes of the present invention will be better understood in connection with the following examples, which are intended as an illustration of and not a limitation upon the scope of the invention as defined in the appended claims.

EXAMPLE 1

N-[4-[N-(acetylglycyl)amino]benzoyl]-L-aspartic Acid

EXAMPLE 1A

A mixture of N-(tert-butoxycarbonyl)-glycine (2.11 g, 12.2 mmol), iso-butyl chloroformate (1.87 mL, 1.44 mole), and N-methyl morpholine (1.60 mL, 1.44 mole) in THF (10 mL) was stirred for 15 minutes at 0° C., treated with a solution of methyl 4-amino benzoate (1.92 g, 12.6 mmol), stirred 16 hours, poured into aqueous $NH_4Cl$, and was extracted with ethyl acetate. The ethyl acetate was washed with water and brine, dried ($MgSO_4$) and concentrated to provide 3.51 g (95%) of the title compound.

MS ($APCI^+$) m/e 309 $(M+H)^+$.

EXAMPLE 1B

A solution of the product of example 1A (3.50 g, 11.3 mmol) and lithium hydroxide monohydrate (2.52 g, 60.0 mmol) in a mixture of 1,4-dioxane (10 mL), isopropanol (10 mL) and water
(8 mL) was stirred at ambient temperature for 16 hours, then evaporated to dryness. The residues were dissolved in water, cooled to 0° C., acidified to pH 5.0 with 1.0M $H_3PO_4$, and extracted with ethyl acetate. The organic phase was washed with water and brine, dried ($MgSO_4$) and concentrated to provide the title compound (3.25 g, 98%).

MS (APCI$^+$) m/e 295 (M+H)$^+$.

EXAMPLE 1C

A solution of the product of example 1B (3.25 g, 11.0 mmol), in hydrogen chloride saturated 1,4-dioxane (50 mL) was stirred at ambient temperature for 1 hour, evaporated to dryness, suspended in ethyl ether then concentrated and vacuum dried to give a white solid (1.94 g).

EXAMPLE 1D

A solution of the product of example 1C (1.94 g, 8.47 mmol), acetyl chloride (0.72 mL, 10.1 mmol) and triethylamine (2.68 mL, 19.2 mmol) in DMF (3 mL) was stirred at ambient temperature for 16 hours, diluted with ethyl acetate then washed sequentially with water and brine, dried ($MgSO_4$), and concentrated to provide the title compound (1.61 g, 83%).

MS (APCI$^+$) m/e 237 (M+H)$^+$.

EXAMPLE 1E

A solution of the product of example 1D (0.44 g, 1.86 mmol), EDCI (0.391 g, 2.05 mmol), L-aspartic acid-($\alpha,\beta$ di-tert-butyl) ester hydrochloride (0.567 g, 2.05 mmol), and N-hydroxybenzotriazole (0.277 g, 2.05 mmol) in THF (20 mL) was cooled to 0° C., stirred for 16 hours, diluted with water (100 mL), and extracted with ethyl acetate. The ethyl acetate was washed with 0.5M HCl, aqueous sodium bicarbonate, and brine, dried ($MgSO_4$), and concentrated to provide a yellow oil which was chromatographed on silica with MeOH/Chloroform to provide the title compound (0.33 g, 38%).

MS (APCI$^+$) m/e 407 (M-t-Bu)$^+$.

EXAMPLE 1F

N-[4-[N-(acetylglycyl)amino]benzoyl]-L-aspartic Acid

The product of example 1E was processed as in example 1C to provide the title compound.

MS (APCI$^+$) m/e 352 (M+H)$^+$;
$^1$H NMR (300 MHz, DMSO-$d_6$) $\delta$ 10.19 (s, 1H), 8.62 (d, 1H), 7.80 (d, 2H), 7.65 (d, 2H), 4.73 (m, 1H), 3.42 (m, 1H), 2.84 (m, 1H), 2.68 (m, 1H), 2.06 (s, 3H).

EXAMPLE 2

4-[[4-(aminomethyl)benzoyl]amino]-2-phenylbenzoic Acid

EXAMPLE 2A

A solution of 4-aminomethylbenzoic acid (5.67 g, 37.5 mmol) triethylamine (5.20 mL, 37.5 mmol) and di-tert-butyl dicarbonate (9.5 mL, 41.2 mmol) in aqueous 1,4-dioxane (1/1) was stirred for 16 hours, reduced in volume under vacuum, cooled to 0° C., acidified with 1M $H_3PO_4$, then extracted with ethyl acetate. The organic phase was washed with water and brine, dried ($MgSO_4$) and evaporated to provide the title compound (8.47 g, 90%).

MS (APCI$^-$) m/e 250 (M–H)$^-$.

EXAMPLE 2B

The product of example 2A and methyl 4-aminomethyl-3-phenyl-benzoate were processed as in examples 1E and 1B to provide the title compound.

MS (APCI$^-$) m/e 445 (M–H)$^-$.

EXAMPLE 2C

4-[[4-(aminomethyl)benzoyl]amino]-2-phenylbenzoic Acid

The product of example 2B was processed as in example 1C to provide the title compound.

MS (APCI$^-$) m/e 381 (M–H)$^-$;
$^1$H NMR (300 MHz, DMSO-$d_6$) $\delta$ 10.58 (s, 1H), 8.42 (m, 3H), 7.98 (m, 3H), 7.83 (m, 1H), 7.62 (m, 2H), 7.38 (m, 4H), 4.12 (m, 2H).

EXAMPLE 3

N-[4-[(7-amino-1-oxoheptyl)amino]benzoyl]-L-aspartic Acid

EXAMPLE 3A 7-(tert-Butoxycarbonylamino)heptanoic acid (0.96 g, 3.91 mmol) and methyl 4-aminobenzoate (0.65 g, 4.30 mmol) were processed as in example 1C to provide the title compound.

MS (APCI$^+$) m/e 379 (M+H)$^+$.

EXAMPLE 3B

The product of example 3A was processed as in example 1B to provide the title compound.

MS (APCI$^+$) m/e 365 (M+H)$^+$.

EXAMPLE 3C

N-[4-[(7-amino-1-oxoheptyl)amino]benzoyl]-L-aspartic Acid

The product of example 3B was processed as in examples 1E and 1F to provide the title compound.

MS (APCI$^+$) m/e 380 (M+H)$^+$;
$^1$H NMR (300 MHz, DMSO-$d_6$) $\delta$ 10.18 (s, 1H), 8.61 (d, 1H), 7.82 (d, 2H), 7.68 (m, 3H), 4.73 (m, 1H), 2.76 (m, 4H), 2.36 (m, 2H), 1.58 (m, 4H), 1.33 (m, 4H).

EXAMPLE 4

(S)-methyl 3-[[6-amino-2-[[(1,1-dimethylethoxy)carbonyl]amino]-1-oxohexyl]amino]-4-(1,1-dimethylethyl)benzoate

EXAMPLE 4A

To a solution of methyl 4-tert butyl benzoate (10.0 g, 52.0 mmol) in concentrated sulfuric acid (25 mL) at 0° C. was added a mixture of concentrated nitric acid (9.7 mL, 155 mmol) in concentrated sulfuric acid (10 mL). The mixture was stirred for 16 hours, poured into ice water (600 mL), and extracted with ethyl acetate. The organic phase was washed with water, aqueous sodium bicarbonate, and brine, dried (MgSO$_4$) evaporated and chromatographed to provide the title compound.

MS (APCI$^+$) m/e 238 (M+H)$^+$.

EXAMPLE 4B

The product of example 4A (12.3 g, 52.2 mmol) and 10% palladium on carbon, (1.0 g) in methyl alcohol (100 mL) was stirred under an atmosphere of hydrogen gas for 24 hours, filtered, evaporated to dryness, crystallized from ethyl acetate/hexane to provide 3.35 g (31%) of the title compound.

EXAMPLE 4C

The product of example 4B and BOC-(ε-CBZ)-L-lysine were processed as in example 1E to provide the title compound.

MS (APCI$^+$) m/e 570 (M+H)$^+$.

EXAMPLE 4D (S)-methyl 3-[[6-amino-2-[[(1,1-dimethylethoxy) carbonyl]amino]-1-oxohexyl]amino]-4-(1,1-dimethylethyl)benzoate The product of example 4C (0.86 g, 1.51 mmol) and 10% palladium on carbon (0.1 g) in methyl alcohol (10 mL) was stirred under an atmosphere of hydrogen gas for 24 hours, filtered, and evaporated to dryness to provide the title compound (0.56 g, 85%).

MS (APCI$^-$) m/e 434 (M−H)$^-$;

$^1$H NMR (300 MHz, DMSO-d$_6$) δ 9.23 (m, 1H), 7.77 (m, 1H), 7.67 (s, 1H), 7.54 (m, 1H), 7.14 (m, 1H), 4.10 (m, 1H), 3.83 (s, 3H), 2.53 (m, 2H), 1.68 (m, 6H), 1.43 (s, 9H), 1.33 (s, 9H).

EXAMPLE 5

(S)-3-[[2-(acetylamino)-6-amino-1-oxohexyl) amino]-4-(1,1-dimethylethyl)benzoic acid The product of example 4C was processed according to examples 1C, 1D and 4D to provide the title compound.

MS (APCI$^-$) m/e 376 (M−H)$^-$;

$^1$H NMR (300 MHz, DMSO-d$_6$) δ 9.32 (m, 1H), 8.18 (m, 1H), 7.78 (m, 1H), 7.62 (s, 1H), 7.54 (m, 1H), 4.46 (m, 1H), 4.33 (s, 3H), 2.62 (m, 2H), 1.90 (s, 3H), 1.48 (m, 6H), 1.33 (s, 9H).

EXAMPLE 6

3-(((2S)-2-(acetylamino)-6-aminohexanoyl)amino)4-(tert-butyl)benzoic Acid

The product of example 4C was processed according to examples 1C, 1D, 1B and 4D to provide the title compound.

MS (APCI$^-$) m/e 362 (M−H)$^-$;

$^1$H NMR (300 MHz, DMSO-d$_6$) δ 9.30 (s, 1H), 8.31 (m, 1H), 7.68 (m, 1H), 7.48 (s, 1H), 7.34 (m, 1H), 4.44 (m, 1H), 2.83 (m, 2H), 1.90 (s, 3H), 1.63 (m, 4H), 1.49 (m, 2H), 1.29 (s, 9H).

EXAMPLE 7

(S)-methyl 4-[[2-[[(1,1-dimethylethoxy)carbonyl] amino]-6-[(phenylmethoxy)carbonyl]amino]-1-oxohexyl]amino]-2-[3-(phenylmethoxy)-phenyl] benzoate

EXAMPLE 7A

A mixture of 1-benzyloxy-2-bromobenzene (12.8 g, 48.7 mmol) and n-butyllithium (55 mmol) in THF (150 mL) was stirred for 20 min at −78° C., treated with tri-iso-propyl borate (34 mL, 147 mmol), stirred for 20 minutes at −78° C., then 30 minutes at ambient temperature. The mixture was reduced in volume by rotary evaporation, diluted with ethyl acetate washed sequentially with 1M HCl (twice), water, and brine, dried (MgSO$_4$) and concentrated to provide a white solid which was triturated with hexanes to provide the title compound as a white powder (7.04 g).

MS (DCI/NH$_3$) m/e 246 (M+NH$_4$)$^+$.

EXAMPLE 7B

A solution of the product of example 7A (3.20 g, 14 mmol), methyl 2-chloro-4-nitro-benzoate (3.20 g, 14.8 mmol), cesium flouride (5.08 g, 33 mmol), and tetrakis (triphenylphosphine) palladium (0.48 g, 0.42 mmol) in dry, degassed dimethoxyethane (50 mL) was heated to 90° C. for 16 hours, diluted with diethyl ether, washed sequentially with water, brine, aqueous NaHCO$_3$, 1M HCl, and brine, dried (MgSO$_4$), and concentrated. The residue was purified by flash chromatography on silica gel with 20% acetone/hexanes to provide the title compound (3.56 g).

MS (DCI/NH$_3$) m/e 381 (M+NH$_4$)$^+$.

EXAMPLE 7C

The product of example 7B (2.46 g, 6.77 mmol), 4M HCl in 1,4-dioxane (1 mL), and 10% palladium on carbon (0.21 g) in methyl alcohol (50 mL) was stirred under an atmosphere of hydrogen gas for 2 hours, filtered, and evaporated to dryness. The residues were neutralized with aqueous Na$_2$CO$_3$, extracted into CH$_2$Cl$_2$, dried (MgSO$_4$), and concentrated to provide the title compound (1.51 g).

MS (DCI/NH$_3$) m/e 351 (M+NH$_4$)$^+$, 334 (M+H)$^+$.

EXAMPLE 7D (S)-methyl 4-[[2-[[(1,1-dimethylethoxy)carbonyl] amino]-6-[(phenylmethoxy)carbonyl]amino]-1-oxohexyl]amino]-2-[3-(phenylmethoxy)phenyl] benzoate The product of example 7C and BOC-(ε-CBZ)-L-lysine were processed as in example 1E to provide the title compound.

MS (APCI$^+$) m/e 713 (M+NH$_4$)$^+$, 696 (M+H)$^+$;

$^1$H NMR (300 MHz, DMSO-d$_6$) δ 10.28 (bds, 1H), 7.70 (s, 1H), 7.66 (d, 1H), 7.4–7.2 (m, 11H), 7.08 (d, 1H), 7.03 (dd, 1H), 6.88 (s, 1H), 6.82 (d, 1H), 5.12 (s, 2H), 4.98 (s, 2H), 4.02 (m, 1H), 3.54 (s, 3H), 2.97 (m, 2H), 1.58 (m, 2H), 1.38 (s, 9H), 1.35–1.25 (m, 4H).

EXAMPLE 8

(S)-1,1-dimethylethyl 4-[[2-[[(1,1-dimethylethoxy) carbonyl]amino]-6-[(phenylmethoxy)carbonyl] amino]-1-oxohexyl]amino]-2-[3-(phenylmethoxy) phenyl]benzoate The product of example 7A and tert-butyl 2-chloro-4-nitro-benzoate were processed according to examples 7B, 7C, and 7D to provide the title compound.

$^1$H NMR (300 MHz, DMSO-d$_6$) δ 10.25 (bds, 1H), 7.70 (s, 1H), 7.66 (d, 1H), 7.4–7.2 (m, 11H), 7.08 (d, 1H), 7.03 (dd, 1H), 6.88 (s, 1H), 6.82 (d, 1H), 5.12 (s, 2H), 4.98 (s, 2H), 4.02 (m, 1H), 2.97 (m, 2H), 1.58 (m, 2H), 1.38 (s, 9H), 1.35–1.25 (m, 4H), 1.18 (s, 9H).

EXAMPLE 9

(R)-methyl 4-[[6-amino-2-[[(1,1-dimethylethoxy) carbonyl]amino]-1-oxohexyl]amino]-2-(3-hydroxyphenyl)benzoate The product of example 7D was processed according to example 4D to provide the title compound.

MS (ESI) m/e 472 (M+H)$^+$;

¹H NMR (300 MHz, DMSO-d₆) δ 7.67 (m, 3H), 7.18 (m, 1H), 7.07 (m, 1H), 6.75 (m, 1H), 6.63 (m, 2H), 4.03 (m, 1H), 3.58 (s, 3H), 2.61 (m, 2H), 1.60 (m, 2H), 1.50–1.28 (m, 4H), 1.38 (s, 9H).

EXAMPLE 10

(R)-methyl 4-[[6-amino-2-[[(1,1-dimethylethoxy)carbonyl]amino]-1-oxohexyl]amino]-2-(2-hydroxyphenyl)benzoate 1-benzyloxy-2-bromobenzene was processed according to examples 7A, 7B, 7C, 7D, and 4D to provide the title compound.

¹H NMR (300 MHz, DMSO-d₆) δ 8.63 (s, 1H), 8.13 (m, 1H), 7.83 (m, 2H), 7.57 (m, 1H), 7.42 (m, 2H), 7.21 (m, 1H), 6.79 (m, 1H), 4.03 (m, 1H), 3.58 (s, 3H), 2.61 (m, 2H), 1.60 (m, 2H), 1.50–1.28 (m, 4H), 1.38 (s, 9H).

EXAMPLE 11

(S)-methyl 4-[[2-amino-6-[[(phenylmethoxy)carbonyl]amino]-1-oxohexyl]amino]-2-[(3-(phenylmethoxy)phenyl]benzoate The product of example 7D (0.365 g, 0.53 mmol) in a mixture of methylene chloride (2 mL) and trifluoroacetic acid (4 mL) was stirred for 150 minutes, concentrated, and partitioned between ethyl acetate and aqueous sodium bicarbonate. The organic phase was dried (MgSO₄) and concentrated to give the title compound as a tan foam (0.300 g).

¹H NMR (300 MHz, DMSO-d₆) δ 7.74 (s, 1H), 7.68 (s, 1H), 7.4–7.2 (m, 11H), 7.04 (m, 2H), 6.92 (m, 1H), 6.82 (m, 1H), 5.12 (d, 2H), 4.98 (d, 2H), 3.53 (m, 1H), 3.52 (s, 3H), 2.97 (m, 2H), 1.45–1.25 (m, 6H).

EXAMPLE 12

(S)-methyl 4-[[2-(acetylamino)-6-[[(phenylmethoxycarbonyl]amino]-1-oxohexyl]amino]-2-[(3-(phenylmethoxy)phenyl]benzoate The product of example 11 was processed according to example 1D to provide the title compound.

MS (ESI) m/e 660 (M+Na)⁺, 638 (M+H)⁺;

¹H NMR (300 MHz, DMSO-d₆) δ 8.17 (d, 1H), 7.74 (s, 1H), 7.73 (d, 1H), 7.67 (d, 1H), 7.50–7.25 (m, 1H), 7.02 (dd, 1H), 6.88 (m, 1H), 6.81 (d, 1H), 5.11 (s, 2H), 4.96 (s, 2H), 4.35 (m, 1H) 3.54 (s, 3H), 2.95 (m, 2H), 1.86 (s, 3H), 1.61 (m, 2H), 1.45–1.35 (m, 4H).

EXAMPLE 13

(S)-1,1-dimethylethyl 4-[[6-amino-2-[[(1,1-dimethylethoxy)carbonyl]amino]-1-oxohexyl]amino]-2-(3-hydroxphenyl)benzoate The product of example 8 was processed according to example 4D to provide the title compound.

MS (ESI) m/e 514 (M+H)⁺; ¹H NMR (300 MHz, DMSO-d₆) δ 10.23 (s, 1H), 7.66 (s, 1H), 7.63 (d, 1H), 7.20 (t, 1H), 7.08 (d, 1H), 6.76 (dd, 1H), 6.66 (d, 1H), 6.62 (d, 1H), 4.03 (m, 1H), 3.10 (m, 2H), 1.61 (m, 2H), 1.49 (m, 2H), 1.47 (s, 9H), 1.45–1.35 (m, 4H), 1.20 (s, 9H); Anal. calcd for C₂₈H₃₉N₃O₆·0.5 H₂O: C, 64.35; H, 7.71; N, 8.04. Found: C, 64.12; H, 7,57, N, 7.78

EXAMPLE 14

(S)-methyl 4-[[2-(acetylamino)-6-amino-1-oxohexyl]amino]-2-(3-hydroxphenyl)benzoate The product of example 12 was processed according to example 4D to provide the title compound.

MS (ESI) m/e 414 (M+H)⁺; ¹H NMR (300 MHz, DMSO-d₆) δ 10.36 (s, 1H), 9.50 (s, 1H), 8.19 (d, 1H), 7.68 (m, 3H), 7.61 (bds, 2H), 7.18 (t, 1H), 6.74 (dd, 1H), 6.63 (m, 2H), 4.37 (m, 1H), 3.57 (s, 3H), 2.77 (m, 2H), 1.88 (s, 3H), 1.62–1.50 (m, 4H), 1.30–1.18 (m, 2H).

EXAMPLE 15

(S)-4-[[2-(acetylamino)-6-amino-1-oxohexyl)amino]-2-(3-hydroxphenyl)benzoic acid The product of example 8 was processed according to examples 11, 1D, and 4D to provide the title compound.

MS (ESI) m/e 400 (M+H)⁺; ¹H NMR (300 MHz, DMSO-d₆) δ 10.33 (s, 1H), 8.22 (s, 1H), 7.60 (m, 3H), 7.61 (m, 1H), 7.16 (t, 1H), 6.73–6.68 (m, 3H), 4.36 (m, 1H), 2.76 (t, 2H), 1.88 (s, 3H), 1.72–1.48 (m, 4H), 1.40–1.28 (m, 2H).

EXAMPLE 16

(S)-N-[4-[[2-(acetylamino)-6-amino-1-oxohexyl]amino]-2-(3-hydroxyphenyl)benzoyl]-L-α-asparagine

EXAMPLE 16A

The product of example 12 was processed according to example 1B to provide the title compound.

MS (ESI) m/e 624 (M+H)⁺.

EXAMPLE 16B (S)-N-[4-[[2-(acetylamino)-6-amino-1-oxohexyl]amino]-2-(3-hydroxyphenyl)benzoyl]-L-α-asparagine The product of example 16A and and L-aspartamide beta-tert-butyl ester hydrochloride was processed according to examples 1E, 4D and 11 to provide the title compound.

MS (ESI) m/e 514 (M+H)⁺;

¹H NMR (300 MHz, DMSO-d₆) δ 10.19 (s, 1H), 8.14 (d, 1H), 7.66 (s, 1H), 7.59 (dd, 1H), 7.43 (d, 1H), 7.14 (m, 1H), 7.06 (bds, 1H), 6.87 (bds, 1H), 6.73 (m, 2H), 4.52 (q, 1H), 4.37 (m, 1H), 3.59 (m, 1H), 2.78 (m, 2H), 2.53 (dd, 1H), 2.38 (dd, 1H), 1.87 (s, 3H), 1.74–1.45 (m, 4H), 1.40–1.35 (m, 2H).

EXAMPLE 17

(S)-N-4-[[2-(acetylamino)-6-amino-1-oxohexyl]amino]-2-phenylbenzoyl]-L-α-asparagine Phenyl boronic acid was processed according to examples 7B, 7C, 7D, 1C, 1D, 1B, 1E, 4D, and 11 to provide the title compound.

MS (ESI) m/e 498 (M+H)⁺;

¹H NMR (300 MHz, CD₃OD) δ 7.88 (m, 2H), 7.55 (d, 1H), 7.40 (m, 5H), 4.73 (m, 1H), 4.46 (m, 1H), 2.93 (m, 2H), 2.56 (m, 2H), 1.97 (s, 3H), 1.74–1.45 (m, 4H), 1.40–1.35 (m, 2H).

EXAMPLE 18

(S)-N-[4-[[2-(acetylamino)-6-amino-1-oxohexyl]amino]benzoyl]-L-α-asparagine

Methyl 4-aminobenzoate was processed according to examples 7D, 1C, 1D, 1B, 1E, 4D, and 11 to provide the title compound.

MS (ESI) m/e 423 (M+H)⁺;

¹H NMR (300 MHz, DMSO-d₆) δ 10.38 (s, 1H), 8.21 (d, 1H), 7.81 (d, 2H), 7.68 (m, 3H), 4.68 (m, 1H), 4.39 (m, 1H), 4.13 (m, 2H), 2.78 (m, 2H), 1.85 (s, 3H), 1.70–1.35 (m, 6H).

EXAMPLE 19

N-[(4-aminophenyl)acetyl]-L-aspartic Acid, Bis(1,1-dimethylethyl) ester 4-nitrophenylacetic acid was processed according to examples 1E and 4D to provide the title compound.

MS (ESI) m/e 379 (M+H)⁺;

¹H NMR (300 MHz, DMSO-d₆) δ 8.09 (d, 1H), 6.88 (d, 2H), 6.46 (d, 2H), 4.78 (s, 2H), 4.45 (m, 1H), 2.61 (dd, 1H), 2.50 (m, 1H), 1.37 (s, 18H);

Anal. calcd for $C_{20}H_{30}N_2O_5$: C, 63.47; H, 7.99; N, 7.40. Found: C, 63.37; H, 7.76; N, 7.30.

EXAMPLE 20

(S)-N-[[4-[[2-amino-6-[[(phenylmethoxy)carbonyl]amino]-1-oxohexyl]amino]phenyl]acetyl]-L-aspartic Acid The product of example 19 and BOC-(ε-CBZ)-L-lysine were processed according to examples 1E and 11 to provide the title compound.

MS (ESI) m/e 529 (M+H)⁺;

¹H NMR (300 MHz, DMSO-d₆) δ 10.39 (s, 1H), 8.42 (d, 1H), 8.21 (bd, 2H), 7.50 (d, 2H), 7.38–7.29 (m, 4H), 7.25–7.15 (m, 3H), 5.97 (s, 2H), 4.51 (d, 1H), 3.88 (m, 1H), 2.99 (q, 2H), 2.69 (dd, 1H), 2.59 (dd, 1H), 1.80 (m, 2H), 1.48–1.32 (m, 4H).

EXAMPLE 21

(S)-N-[[4-[[2-(acetylamino)-6-[[(phenylmethoxy)carbonyl]amino]-1-oxohexyl]amino]phenyl]acetyl]-L-aspartic Acid The product of example 20 was processed according to example 1D to provide the title compound.

MS (ESI) m/e 551 (M+H)⁺;

¹H NMR (300 MHz, DMSO-d₆) δ 9.93 (s, 1H), 8.33 (d, 1H), 8.07 (d, 1H), 7.48 (d, 2H), 7.32 (m, 4H), 7.21 (m, 1H), 7.15 (d, 2H), 4.99 (s, 2H), 4.52 (m, 1H), 4.32 (m, 1H), 3.41 (s, 3H), 2.97 (m, 2H), 2.69 (dd, 1H), 2.57 (dd, 1H), 1.70–1.50 (m, 2H), 1.45–1.25 (m, 4H).

EXAMPLE 22

N-[2-[[4-[2-(acetylamino)-6-amino-1-oxohexyl]amino]phenyl]-1-oxoethyl]-L-aspartic Acid The product of example 21 was processed according to example 4D to provide the title compound.

MS (ESI) m/e 437 (M+H)⁺;

¹H NMR (300 MHz, DMSO-d₆) δ 10.00 (s, 1H), 8.37 (d, 1H), 8.16 (d, 1H), 7.65 (bds, 2H), 7.49 (d, 2H), 7.17 (d, 2H), 4.50 (m, 1H), 4.37 (m, 1H), 3.40 (s, 3H), 2.78 (m, 2H), 2.68 (dd, 1H), 2.57 (dd, 1H), 1.70–1.60 (m, 2H), 1.60–1.45 (m, 4H).

EXAMPLE 23

(S)-N-[[4-[[6-amino-2-[[(1,1-dimethylethoxy)carbonyl]amino]-1-oxohexyl]amino]phenyl]acetyl]-L-aspartic Acid, Bis(1,1-dimethylethyl)ester The product of example 19 and BOC-(ε-CBZ)-L-lysine were processed according to examples 1E and 4D to provide the title compound.

MS (ESI) m/e 607 (M+H)⁺;

¹H NMR (300 MHz, DMSO-d₆) δ 9.93 (s, 1H), 8.37 (d, 1H), 7.52 (d, 2H), 7.17 (d, 2H), 4.45 (q, 1H), 4.02 (m, 1H), 3.58 (m, 2H), 3.40 (s, 2H), 2.66 (dd, 1H), 2.53 (dd, 1H), 1-68–1.53 (m, 4H), 1.38 (bds, 27H), 1.30 (m, 2H);

Anal. calcd for $C_{31}H_{50}N_4O_8 \cdot 0.75\ C_4H_8O_2$: C, 57.57; H, 8.10; N, 7.90. Found: C, 57.99; H, 8.04; N, 7.57.

EXAMPLE 24

(S)-N-[[4-[(2,6-diamino-1-oxohexyl)amino]phenyl]acetyl]-L-aspartic Acid

The product of example 23 was processed according to example 11 to provide the title compound.

MS (ESI) m/e 395 (M+H)⁺;

¹H NMR (300 MHz, DMSO-d₆) δ 10.48 (d, 1H), 8.43 (d, 1H), 8.25 (m, 2H), 7.67 (bds, 2H), 7.52 (d, 2H), 7.22 (d, 2H), 4.51 (m, 1H), 3.90 (m, 1H), 3.44 (s, 2H), 2.77 (m, 2H), 2.69 (dd, 1H), 2.59 (dd, 1H), 1.80 (m, 2H), 1.70–1.50 (m, 4H);

Anal. calcd for $C_{18}H_{26}N_4O_6 \cdot 2.0\ C_2HF_3O_2$: C, 42.45; H, 4.53; N, 9.00. Found: C, 42.23; H, 4.70; N, 7.73.

EXAMPLE 25

(S)-ethyl 4-[[6-amino-2-[[(1,1-dimethylethoxy)carbonyl]amino]-1-oxohexyl]amino]benzeneacetate Monohydrochloride Ethyl 4-aminophenylacetate and BOC-(ε-CBZ)-L-lysine were processed according to examples 1E and 4D to provide the title compound, which was isolated as its hydrochloride salt.

MS (ESI) m/e 408 (M+H)⁺;

¹H NMR (300 MHz, CD₃OD) δ 9.80 (bds, 1H), 7.50 (d, 2H), 7.23 (d, 2H), 4.17 (m, 1H), 4.12 (q, 2H), 3.69 (m, 2H), 3.49 (s, 2H), 2.91 (m, 2H), 1.85–1.65 (m, 4H), 1.42 (s, 9H), 1.22 (t, 3H);

Anal. calcd for $C_{21}H_{34}ClN_3O_5 \cdot 0.33\ C_4H_{10}O$: C, 57.23; H, 8.03; N, 8.97. Found: C, 57.23; H, 7.75; N, 8.92.

EXAMPLE 26

(S)-4-[[6-amino-2-[[(1,1-dimethylethoxy)carbonyl]amino]-1-oxohexyl]amino]benzeneacetic Acid Ethyl 4-aminophenylacetate and BOC-(ε-CBZ)-L-lysine were processed according to examples 1E, 1B and 4D to provide the title compound, which was isolated as its hydrochloride salt.

MS (ESI) m/e 380 (M+H)⁺;

¹H NMR (300 MHz, DMSO-d6) δ 9.97 (s, 1H), 7.53 (d, 2H), 7.18 (d, 2H), 4.05 (m, 1H), 3.50 (s, 2H), 2.77 (m, 2H), 1.66–1-50 (m, 4H), 1.30–1.22 (m, 2H);

Anal. calcd for $C_{19}H_{29}ClN_3O_5 \cdot C_4H_{10}O$: C, 56.61; H, 7.85; N, 8.61. Found: C, 56.68; H, 7.84; N, 6.86.

EXAMPLE 27

Methyl 5-(((2S)-6-amino-2-((tert-butoxycarbonyl)amino)hexanoyl)amino)-4'-hydroxy(1,1'-biphenyl)-2-carboxylate 1-Benzyloxy-4-bromobenzene was processed according to examples 7A, 7B, 7C, 7D and 4D to provide the title compound.

MS (FAB) m/e 472 (M+H)⁺, 470 (M−H)⁺;

¹H NMR (300 MHz, DMSO-d6) δ 7.71–7.62 (m, 3H), 7.15 (d, 1H), 7.09–7.03 (m, 2H), 6.82–6.77 (m, 2H), 4.09–4.02 (m, 1H), 3.57 (s, 3H), 2.70–2.65 (m, 2H), 1.70–1.24 (m, 15H, includes 1.40, s).

EXAMPLE 28

(3S)-3-(((5-(((2S)-2-(acetylamino)-6-aminohexanoyl)amino)-4'-hydroxy(1,1'-biphenyl)-2-yl)carbonyl)amino)-4-amino-4-oxobutanoic Acid 1-Benzyloxy-4-bromobenzene was processed according to examples 7A, 7B, 7C, 7D, 1B, 1E, and 11 to provide the title compound.

MS (FAB) m/e 514 (M+H)$^+$;

¹H NMR (300 MHz, MeOH-d4) δ 7.65–7.59 (m, 2H), 7.65–7.59 (m, 2H), 7.53–7.48 (m, 1H), 7.16–7.12 (m, 2H), 6.85–6.80 (m, 2H), 4.77–4.73 (m, 1H), 4.52–4.45 (m, 1H), 3.03–2.88 (m, 2H), 2.88–2.57 (m, 2H), 2.02 (s, 3H), 1.96–1.64 (m, 4H), 1.56–1.46 (m, 2H).

EXAMPLE 29

Methyl 3-(((2S)-6-amino-2-((tert-butoxycarbonyl)amino)hexanoyl)amino)-4-cyclohexylbenzoate

EXAMPLE 29A

4-Cyclohexylbenzoic acid (10.213 g, 50 mmol) was suspended in 100 mL of methyl alcohol and 1 mL of concentrated sulfuric acid. It then gently refluxed for 15 hours under nitrogen atmosphere. Methanol was removed and the residue was redissolved in 200 mL of diethyl ether. The solution was washed with 30 mL of 10%-sodium hydrogen carbonate (3×), brine (3×), dried (MgSO$_4$) and concentrated to give methyl cyclohexylbenzoate (9.88 g).

MS (DCI+Q1MS) m/e 219 (M+H)$^+$, 236 (M+NH$_4$)$^+$, 253 (M+2NH$_4$—H)$^+$.

EXAMPLE 29B

To a stirred 0° C. cold solution of 5 mL of concentrated sulfuric acid in an ice bath was added the product of example 29A (2.22 g, 10.2 mmol) over 5 minutes. Concentrated nitric acid (2 mL, 32 mmol) in 2 mL of concentrated sulfuric acid was then added in period of 20 minutes., stirred for an additional 30 minutes at 0° C. The mixture was poured into 200 mL of ice-water and the product was extracted with ethyl acetate. The ethyl acetate layer was washed with 10%-sodium hydrogen carbonate (2×), brine (2×), water, dried (MgSO$_4$) and evaporated to yield 2.5 g of methyl 4-cyclohexyl-3-nitro-benzoate.

MS (DCI+Q1MS) m/e 281 (M+NH$_4$)$^+$, 298 (M+2NH$_4$—H)+.

EXAMPLE 29C

The compound of example 29B (2.07 g, 7.86 mmol) was processed as in examples 7C, 7D, and 4D to yield the title compound.

MS (ESI+Q1MS) m/e 462 (M+H)$^+$, 406 (M+H-Bu$^t$)$^+$, 362 (M+H-Boc)$^+$, 923 (2M+H)$^+$;

¹H NMR (300 MHz, DMSO-d6) δ 9.52 (bds, 1H), 7.81 (s, 1H), 7.76 (dd, 1H), 7.42 (d, 1H), 7.06 (d, 1H), 4.09 (m, 1H), 3.81 (s, 3H), 3.12 (m, 1H), 2.82 (m, 2H), 1.80–1.50 (m, 6H), 1.38 (s, 9H), 1.40–1.25 (m, 10H).

EXAMPLE 30

Tert-butyl (3S)-3-(((5-(((2S)-2-(acetylamino)-6-aminohexanoyl)amino)-3'-hydroxy(1,1'-biphenyl)-2-yl)carbonyl)amino)-4-amino-4-oxobutanoate The product of example 16A and and L-aspartamide beta-tert-butyl ester hydrochloride was processed according to examples 1E and 4D to provide the title compound.

MS (ESI) m/e 570 (M+H)$^+$;

¹H NMR (300 MHz, MeOH-d4) δ 9.91 (bds, 1H), 8.28 (d, 1H), 8.17 (d, 1H), 7.63 (m, 2H), 7.42 (d, 1H), 7.12 (m, 2H), 6.88 (bds, 1H), 6.77 (s, 1H), 6.71 (m, 1H), 4.56 (m, 1H), 4.35 (m, 1H), 2.63 (m, 2H), 2.55 (dd, 1H), 2.36 (dd, 1H), 1.87 (s, 3H), 1.38 (s, 9H), 1.60–1.30 (m, 6H).

EXAMPLE 31

5-(((2S)-6-amino-1-(tert-butoxycarbonyl)aminohexanoyl)amino)-3'-hydroxy(1,1'-biphenyl)-2-carboxylic Acid

EXAMPLE 31A

A mixture of 2-chloro-4-nitrobenzoic acid (2.11 g, 12.2 mmol), K$_2$CO$_3$ (2.1 g. 15 mmol) and benzyl bromide (14 mL, 12.0 mmol) in acetone (250 mL) was stirred for 6 hours at 60° C., cooled, filtered and concentrated. The residues were redissolved in ethyl ether, washed with aqueous Na$_2$CO$_3$ and brine, dried (MgSO$_4$) and concentrated to provide 23 g (66%) of the title compound.

MS (ESI) m/e 292 (M+H)$^+$.

EXAMPLE 31B

The product of example 31A and the product of example 7A were processed according to the method of example 7B to give the title compound.

MS (ESI) m/e 440 (M+H)$^+$.

EXAMPLE 31C

The product of example 31B (11.11 g, 25.3 mmol) and stannous chloride (24 g, 127 mmol) in a mixture of CH$_2$Cl$_2$ (230 mL) and methanol (20 mL) was stirred for 76 hours at 25° C., treated with 1 M NaOH (200 mL) and stirred a further 1 h. The emulsion was filtered through Celite and the organic phase collected, washed with 1M NaOH, dried (MgSO$_4$) and concentrated to provide 9.2 g (89%) of the title compound.

MS (ESI) m/e 410 (M+H)$^+$.

EXAMPLE 31D

The product of example 31C (7.47 g, 18.3 mmol) and BOC-(ε-CBZ)-L-lysine (6.20 g, 16.3 mmol) in EtOAc (20 mL) was treated with pyridine (0.65 mL, 8.0 mmol) and di-tert-butyl dicarbonate (4.96 g, 22.8 mmol), stirred for 16 hours at 25° C., diluted with EtOAc, washed with brine, 0.5 M citric acid, aqueous NaHCO$_3$ and brine, dried (MgSO$_4$) and concentrated to provide a yellow oil which was chromatographed on silica with acetone/CH$_2$Cl$_2$ to provide the title compound (7.60 g, 60%).

MS (ESI) m/e 772 (M+H)$^+$.

EXAMPLE 31E

The product of example 31D was processed according to example 4D to provide the title compound.

MS (ESI) m/e 458 (M+H)$^+$;

¹H NMR (300 MHz, MeOH-d4) δ 7.57 (d, 1H), 7.46 (m, 2H), 7.15 (t, 1H), 6.93 (m, 2H), 6.71 (m, 1H), 4.17 (m, 1H), 2.88 (m, 2H), 1.68 (m, 6H), 1.43 (s, 9H).

EXAMPLE 32

Methyl 5-(((2S)-2,6-diaminohexanoyl)amino)-3'-hydroxy(1,1'-biphenyl)-2-carboxylate The product of example 9 was processed according to example 1C to provide the title compound.

MS (ESI) m/e 372 (M+H)$^+$;

¹H NMR (300 MHz, MeOH-d4) δ 7.72 (m, 3H), 7.19 (t, 1H), 6.78(m, 1H), 6.70 (m, 2H), 4.08 (m, 1H), 3.68 (m, 2H), 3.67 (s, 3H), 2.01 (m, 2H), 1.83 (m, 2H), 1.53 (m, 2H).

EXAMPLE 33

5-(((2S)-6-amino-2-((2,2-dimethylpropanoyl)amino) hexanoyl)amino)-3'-hydroxy(1,1'-biphenyl)-2-carboxylic Acid

EXAMPLE 33A

The product of example 31D was processed according to the method of example 11 to give the title compound.

MS (ESI) m/e 672 (M+H)⁺.

EXAMPLE 33B

The product of example 33A (0.43 g, 0.64 mmol), trimethylacetyl chloride (0.1 mL, 0.8 mmol) and NMM (0.1 mL, 0.9 mmol) in $CH_2Cl_2$ (15 mL) was stirred at ambient temperature for 16 hours, then washed sequentially with 1 M HCl, and aqueous $NaHCO_3$, dried ($MgSO_4$), and concentrated to provide a yellow foam which was chromatographed on silica with acetone/$CH_2Cl_2$ to provide the title compound (0.16 g, 33%).

MS (ESI) m/e 756 (M+H)⁺.

EXAMPLE 33C

The product of example 33B was processed according to example 4D to provide the title compound.

MS (ESI) m/e 442 (M+H)⁺;

¹H NMR (300 MHz, MeOH-d4) δ 7.56 (m, 1H), 7.48 (m, 2H), 7.15 (m, 1H), 6.92 (m, 2H), 6.72 (m, 1H), 4.52 (m, 1H), 2.79 (m, 2H), 1.80 (m, 2H), 1.45 (m, 4H), 1.22 (s, 9H).

EXAMPLE 34

Methyl 5-(((2S)-6-amino-2-((2,2-dimethylpropanoyl)amino)hexanoyl)amino)-3'-hydroxy(1,1'-biphenyl)-2-carboxylate The product of example 33 (0.045 g, 0.64 mmol) and 18 M HCl (0.4 mL) in 2,2-dimethoxypropane (4 mL) was stirred at ambient temperature for 16 hours, then evaporated to dryness, triturated with ether, and vacuum dried to provide the title compound (0.046 g, 92%).

MS (ESI) m/e 465 (M+H)⁺;

¹H NMR (300 MHz, MeOH-d4) δ 10.25 (s, 1H), 8.57 (d, 1H), 8.12 (d, 1H), 7.81 (d, 2H), 7.68 (d, 2H), 4.70 (m, 1H), 4.35 (m, 1H), 4.08 (m, 1H), 3.00 (m, 1H), 2.82 (dd, 1H), 2.67 (dd, 1H), 1.88 (s, 3H), 1.77 (s, 3H), 1.62 (m, 2H), 1.43 (m, 4H). Anal. calcd for $C_{21}H_{28}N_4O_8 \cdot HCl \cdot H_2O$: C, 52.28; H, 6.27; N, 11.61. Found: C, 52.52; H, 6.45; N, 11.50.

EXAMPLE 35

5-(((2S)-6-amino-2-(benzoylamino)hexanoyl) amino)-3'-hydroxy(1,1'-biphenyl)-2-carboxylic acid The product of example 33A and benzoyl chloride were processed according to examples 33B and 4D to provide the title compound.

¹H NMR (300 MHz, MeOH-d4) δ 7.88 (m, 1H), 7.63 (m, 1H), 7.56 (m, 1H), 7.45 (m, 2H), 7.30 (m, 7H), 3.51 (m, 1H), 2.93 (m, 2H), 1.95 (m, 2H), 1.55 (m, 4H).

EXAMPLE 36

5-(((2S)-6-amino-2-((methoxycarbonyl) aminohexanoyl)amino)-3'-hydroxy(1,1'-biphenyl)-2-carboxylic acid The product of example 33A and methyl chloroformate were processed according to examples 33B and 4D to provide the title compound.

MS (ESI) m/e 416 (M+H)⁺; ¹H NMR (300 MHz, MeOH-d4) δ 7.54 (d, 1H), 7.43 (m, 2H), 7.13 (t, 8H), 6.94 (m, 2H), 6.70 (dd, 1H), 4.23 (m, 1H), 3.63 (s, 3H), 2.88 (m, 2H), 1.77 (m, 2H), 1.48 (m, 4H).

EXAMPLE 37

(4S)-4-((4-(((2S)-2-(acetylamino)-6-aminohexanoyl) amino)benzoyl)amino)-5-(methylamino)-5-oxopentanoic acid

EXAMPLE 37A

Methyl 4-aminobenzoate was processed according to examples 7D, 1C, 1D, 1B to provide the title compound.

MS (ESI) m/e 442 (M+H)⁺.

EXAMPLE 37B

The product of example 37A and L-glutamic acid δ-tert-butyl ester, N-methylamide were processed according to examples 1E, 4D, and 1C to provide the title compound.

MS (ESI) m/e 450 (M+H)⁺; ¹H NMR (300 MHz, MeOH-d4) 67 7.94 (d, 1H), 7.85 (d, 2H), 7.69 (d, 2H), 4.51 (m, 1H), 2.92 (m, 2H), 2.72 (d, 3H), 2.45 (m, 1H), 2.36 (m, 1H), 2.17 (m, 1H), 2.03 (s, 3H), 1.98 (m, 2H), 1.75 (m, 2H), 1.50 (m, 4H).

EXAMPLE 38

4-(((2S)-6-amino-2-((tert-butoxycarbonyl)amino) hexanoyl)amino)benzoic Acid

Methyl 4-aminobenzoate was processed according to examples 7D, 1B and 4D to provide the title compound.

MS (ESI) m/e 366 (M+H)⁺; ¹H NMR (300 MHz, MeOH-d4) 67 10.18 (bds, 1H), 7.81 (d, 2H), 7.56 (d, 2H), 7.13 (d, 1H), 4.06 (m, 1H), 2.70 (m, 2H), 1.60 (m, 2H), 1.50 (m, 4H), 1.39 (s, 9H). Anal. calcd for $C_{18}H_{27}N_3O_5 \cdot 1.5H_2O$: C, 55.09; H, 7.70; N, 10.71. Found: C, 54.84; H, 7.78; N, 10.38.

EXAMPLE 39

(3S)-3-((4-(((2S)-2-(acetylamino)-6-aminohexanoyl) amino)benzoyl)amino)-4-amino-4-oxobutanoic acid The product of example 37A and L-aspartamide β-tert-butyl ester were processed according to examples 1E, 11, and 4D to provide the title compound which was isolated as its HCl salt.

MS (ESI) m/e 421 (M+H)⁺; ¹H NMR (300 MHz, MeOH-d4) 67 7.83 (d, 2H), 7.68 (d, 2H), 4.94 (dd, 1H), 4.49 (m, 1H), 2.93 (m, 3H), 2.82 (dd, 7, 16H), 2.20 (s, 3H), 1.70 (m, 4H), 1.47 (m, 2H). Anal. calcd for $C_{19}H_{27}N_5O_6 \cdot HCl \cdot 1.5 CH_4O$: C, 49.03; H, 6.58; N, 14.29. Found: C, 48.99; H, 6.25; N, 14.23.

EXAMPLE 40

Methyl 4-(((2S)-6-amino-2-((tert-butoxycarbonyl) amino)hexanoyl)amino)benzoate

Methyl 4-aminobenzoate was processed according to examples 7D and 4D to provide the title compound.

MS (ESI) m/e 380 (M+H)⁺; ¹H NMR (300 MHz, MeOH-d4) 67 10.30 (s, 1H), 7.91 (d, 2H), 7.73 (d, 2H), 7.08 (d, 18H), 4.07 (m, 1H), 3.82 (s, 3H), 3.10 (m, 2H), 1.60 (m, 4H), 1.48 (m, 2H), 1.38 (s, 9H).

EXAMPLE 41

Methyl 5-(((2S)-2-((tert-butoxycarbonyl)amino)
hexanoyl)amino-3'-hydroxy(1,1'-biphenyl)-2-
carboxylate Methyl 4-[N-acetyl-L-norleucyl]-amino-2-
(3'hydroxyphenyl)benzoate The product of example 7C and N-(tert-butoxycarbonyl)-norleucine were processed as in examples 1E and 4D to provide the title compound.

MS (ESI-Q1MS) m/e 455 (M−H)$^+$, 911 (2M−H)$^+$; $^1$H NMR (300 MHz, MeOH-d4) δ 7.76–7.60 (m, 2H), 7.22–7.10 (m, 1H), 6.78–6.64 (m, 4H), 4.16–4.12 (m, 1H), 3.61 (s, 3H), 1.85–1.32 (m, 17H, includes 1.45 s, 9H), 0.94 (brt, 3H).

EXAMPLE 42

4-(((2S)-6-amino-2-((tert-butoxycarbonyl)amino)
hexanoyl)amino)-2-chlorobenzoic Acid The product of example 31A was processed according to examples 31C, 31D and 4D, then recrystallized form 1:1 acetonitrile water to provide the title compound.

MS (ESI) m/e 400, 402 (M+H)$^+$; $^1$H NMR (300 MHz, MeOH-d4) δ 7.73 (d, 1H), 7.42 (d, 1H), 7.37 (dd, 1H), 4.16 (m, 1H), 2.92 (t, 2H), 1.68 (m, 2H), 1.53–1.37 (m, 13H, includes 1.45, s, 9H). Anal. calcd for $C_{18}H_{26}ClN_3O_5 \cdot 0.25H_2O$: C, 53.46; H, 6.61; N, 10.39. Found: C, 53.16; H, 6.77; N, 10.74.

EXAMPLE 43

5-(((2S)-2-(acetylamino)-6-aminohexanoyl)amino)-
N-(2-hydroxyphenyl)(1,1'-biphenyl)-2-carboxamide

EXAMPLE 43A

Phenyl boronic acid was processed according to examples 7B, 7C, 7D, 1C, 1D, and 1B to provide the title compound.

MS (ESI+Q1MS) m/e 475 (M+H)$^+$.

EXAMPLE 43B

The product of example 43A and 2-aminophenol were processed according to examples 1E and 4D to provide the title compound.

MS (ESI+Q1MS) m/e 475 (M+H)$^+$, 497 (M+Na)$^+$, 949 (2M+H)$^+$; $^1$H NMR (300 MHz, MeOH-d4) δ 7.75–7.71 (m, 3H), 7.53–7.33 (m, 6H), 6.97–6.92 (m, 1H), 6.78–6.73 (m, 2H), 4.53–4.47 (m, 1H), 2.94 (br t, 2H), 2.03 (s, 3H), 1.97–1.43 (m, 6H).

EXAMPLE 44

5-(((2S)-2-(acetylamino)-6-aminohexanoyl)amino)-
N-(3-hydroxyphenyl)(1,1'-biphenyl)-2-carboxamide The product of example 43A and 3-aminophenol were processed according to examples 1E and 4D to provide the title compound.

MS (ESI+Q1MS) m/e 475 (M+H)$^+$, 497 (M+Na)$^+$; 1H NMR (300 MHz, MeOH-d4) δ 7.75–7.56 (m, 3H), 7.49–7.30 (m, 5H), 7.05–6.96 (m, 2H), 6.74–6.67 (m, 1H), 6.65–6.47 (m, 1H), 4.53–4.47 (m, 1H), 2.94 (t, 2H), 2.03 (s, 3H), 1.97–1.43 (m, 6H).

EXAMPLE 45

5-(((2S)-2-(acetylamino)-6-aminohexanoyl)amino)-
N-(4-hydroxyphenyl)(1,1'-biphenyl)-2-carboxamide The product of example 43A and 4-aminophenol were processed according to examples 1E and 4D to provide the title compound.

MS (ESI+Q1MS) m/e 475 (M+H)$^+$; $^1$H NMR (300 MHz, MeOH-d4) δ 7.78–7.31 (m, 8H), 7.15–7.07 (m, 2H), 6.69–6.65 (m, 2H), 4.53–4.47 (m, 1H), 2.94 (brt, 2H), 2.03 (s, 3H), 1.96–1.43 (m, 6H).

EXAMPLE 46

Methyl 5-(((2S)-6-amino-2-(((benzyloxy)carbonyl)
amino)hexanoyl)amino)(1,1'-biphenyl)-2-
carboxylate

EXAMPLE 46A

Phenyl boronic acid was processed according to examples 7B and 7C to provide the title compound.

MS (ESI+Q1MS) m/e 215 (M+H)$^+$.

EXAMPLE 46B

The product of example 46A and N-alpha-benzyloxycarbonyl-N-epsilon-tert-butoxycarbonyl-L-lysine were processed according to example 1E to provide the title compound.

MS (ESI-Q1MS) m/e 588 (M−H)$^+$, 624 (M+2NH$_4$—H)$^+$.

EXAMPLE 46C

The product of example 46B was processed according to example 1C to provide the title compound.

MS (ESI+Q1MS) m/e 490 (M+H)$^+$, 979 (2M+H)$^+$; $^1$H NMR (300 MHz, MeOH-d4) δ 7.80–7.61 (m, 3H); 7.43–7.24 (m, 10H), 5.10 (s, 2H), 4.29–4.24 (m, 1H), 3.58 (s, 3H), 2.92 (t, 2H), 1.95–1.44 (m, 6H).

EXAMPLE 47

5-(((2S)-2-((tert-butoxycarbonyl)amino)-6-((3-
pyridinylcarbonyl)amino)hexanoyl)amino)-3'-
hydroxy(1,1'-biphenyl)-2-carboxylic acid The product of example 31B and N-alpha-tert-butoxycarbonyl-N-epsilon-3-pyridylcarbonyl-L-lysine were processed according to examples 31D and 4D to provide the title compound.

MS (ESI) m/e 563 (M+H)$^+$; $^1$H NMR (300 MHz, MeOH-d4) δ 9.93 (d, 1H), 8.63 (dd, 1H), 8.17 (dt, 1H), 7.72 (m, 2H), 7.62 (m, 1H), 7.58 (m, 1H), 7.48 (m, 1H), 7.18 (m, 1H), 6.78 (m, 2H), 4.05 (m, 1H), 3.42 (m, 1H), 3.24 (m, 1H), 1.78 (m, 2H), 1.67 (m, 2H), 1.53 (m, 2H), 1.42 (s, 9H). Anal. calcd for $C_{30}H_{34}N_4O_7$: C, 64.04; H, 6.09; N, 9.96. Found: C, 63.75; H, 6.43; N, 9.69.

EXAMPLE 48

5-(((2S)-2-(acetylamino)-6-aminohexanoyl)amino)
(1,1'-biphenyl)-2-carboxylic Acid

EXAMPLE 48A

2-Chloro-4-nitrobenzoic acid (27.21 g, 135 mmol), concentrated $H_2SO_4$ (2.6 mL) and isobutylene (125 mL) in $CH_2Cl_2$ (125 mL) were shaken in a sealed reaction vessel at ambient temperature for 16 hours, diluted with EtOAc, then washed with aqueous NaHCO$_3$, dried (MgSO$_4$), and concentrated to provide the title compound (33.67 g, 97%).

MS (ESI+Q1MS) m/e 258, 260 (M+H)$^+$.

EXAMPLE 48B

The product of example 48A and phenyl boronic acid were processed according to example 7B to provide the title compound.

MS (ESI+Q1MS) m/e 300 (M+H)$^+$.

EXAMPLE 48C

The product of example 48B (10.37 g, 34.7 mmol) and 10% Pd on charcoal (1 g) in EtOAc (200 mL) were shaken under hydrogen (4 atm) in a sealed reaction vessel at ambient temperature for 23 hours, filtered, and concentrated to provide the title compound (8.51 g, 91%).

MS (ESI+Q1MS) m/e 270 (M+H)$^+$.

EXAMPLE 48D

The product of example 48C was processed according to examples 31D, 11, 1D and 4D to provide the title compound.

MS (ESI) m/e 384 (M+H)$^+$; $^1$H NMR (300 MHz, MeOH-d4) δ 7.77 (d, 1H), 7.63 (dd, 1H), 7.59 (d, 1H), 7.33 (m, 5H), 4.49 (dd, 1H), 2.92 (t, 2H), 2.01 (s, 3H), 1.89 (m, 1H), 1.77 (m, 1H), 1.69 (m, 2H), 1.48 (m, 2H).

EXAMPLE 49

5-((6-aminohexanoyl)amino)-3'-hydroxy(1,1'-biphenyl)-2-carboxylic Acid

The product of example 31C and 6-(carbonylbenzyloxy) amino-hexanoic acid were processed according to examples 31D and 4D to provide the title compound.

MS (ESI) m/e 343 (M+H)$^+$; $^1$H NMR (300 MHz, MeOH-d4) δ 7.78 (d, 1H), 7.64 (dd, 1H), 7.49 (d, 1H), 7.18 (m, 1H), 6.76 (m, 2H), 2.94 (t, 2H), 2.44 (t, 2H), 1.72 (m, 4H), 1.46 (m, 2H). Anal. calcd for C$_{19}$H$_{22}$N$_2$O$_4$.HCl: C, 60.24; H, 6.12; N, 7.39. Found: C, 59.87; H, 6.43; N, 7.19.

EXAMPLE 50

5-(((2S)-2-((tert-butoxycarbonyl)amino)hexanoyl) amino)-3'-hydroxy(1,1'-biphenyl)-2-carboxylic Acid The product of example 31C and N-(tert-butoxycarbonyl)-norleucine were processed according to examples 31D and 4D to provide the title compound.

MS (ESI) m/e 443 (M+H)$^+$; $^1$H NMR (300 MHz, MeOH-d4) δ 7.77 (d, 1H), 7.66 (m, 1H), 7.58 (d, 1H), 7.16 (m, 1H), 6.76 (m, 3H), 4.13 (m, 1H), 1.77 (m, 1H), 1.67 (m, 1H), 1.43 (s, 9H), 1.39 (m, 2H), 0.93 (t, 3H). Anal. calcd for C$_{24}$H$_{30}$N$_2$O$_6$: C, 65.14; H, 6.83; N, 6.33. Found: C, 65.44; H, 6.88; N, 6.61.

EXAMPLE 51

5-(((2S)-5-amino-2-((tert-butoxycarbonyl)amino) pentanoyl)amino)-3'-hydroxy(1,1'-biphenyl)-2-carboxylic acid The product of example 31C and BOC-(δ-CBZ)-L-ornithine were processed according to examples 31D and 4D to provide the title compound.

MS (ESI) m/e 444 (M+H)$^+$; $^1$H NMR (300 MHz, MeOH-d4) δ 7.78 (d, 1H), 6.67 (m, 1H), 7.61 (d, 1H), 7.17 (m, 1H), 6.78 (m, 2H), 4.23 (m, 1H), 2.97 (m, 2H), 1.90 (m, 1H), 1.77 (m, 3H), 1.43 (s, 9H). Anal. calcd for C$_{23}$H$_{29}$N$_3$O$_6$.HCl: C, 57.56; H, 6.30; N, 8.75. Found: C, 57.49; H, 6.54; N, 8.36.

EXAMPLE 52

(2S)-2-(((5-(((2S)-2-(acetylamino)-6-aminohexanoyl)amino)(1,1'-biphenyl)-2-yl) carbonyl)amino)butanedioic Acid The product of example 43A and L-aspartic acid dibenzyl ester were processed according to examples 1E and 4D to provide the title compound, which was isolated as its HCl salt.

MS (ESI) m/e 499 (M+H)$^+$; $^1$H NMR (300 MHz, MeOH-d4) δ 7.68 (m, 2H), 7.52 (m, 1H), 7.39 (m, 5H), 4.76 (m, 1H), 4.48 (m, 1H), 2.93 (m, 2H), 2.69 (m, 2H), 2.03 (s, 3H), 1.92 (m, 1H), 1.70 (m, 3H), 1.50 (m, 2H). Anal. calcd for C$_{23}$H$_{29}$N$_3$O$_6$.HCl.0.6H$_2$O: C, 54.91; H, 6.12; N, 10.25. Found: C, 55.39; H, 6.15; N, 9.86.

EXAMPLE 53

5-(((2S)-2-((tert-butoxycarbonyl)amino)-6-(methylamino)hexanoyl)amino)-3'-hydroxy(1,1'-biphenyl)-2-carboxylic acid

EXAMPLE 53A (N-ε-Methyl)-L-lysine hydrochloride (1.0 g, 5.1 mmol) and di-(tert-butyl)dicarbonate (1.18 g, 5.4 mmol) in dioxane (25 mL) and 1 M NaOH (12 mL) were stirred at ambient temperature for 30 minutes, treated with benzyl chloroformate (2.21 g of 50 weight % solution in toluene, 6.5 mmol) and 1M NaOH (7 mL), stirred a further 30 minutes, diluted with ether, then washed with 1M NaHSO$_4$, dried (MgSO$_4$), and concentrated to provide the title compound.

MS (ESI+Q1MS) m/e 395 (M+H)$^+$.

EXAMPLE 53B

The crude product of example 53A and the product of example 31C were processed according to examples 31D and 4D to provide the title compound after preparative HPLC purification.

MS (ESI) m/e 472 (M+H)$^+$; $^1$H NMR (300 MHz, MeOH-d4) δ 7.60 (m, 1H), 7.55 (d, 1H), 7.15 (m, 2H), 6.92 (m, 2H), 6.72 (m, 1H), 3.68 (m, 1H), 3.34 (s, 3H), 3.24 (m, 2H), 1.92 (m, 2H), 1.60 (m, 4H), 1.46 (s, 9H). Anal. calcd for C$_{25}$H$_{33}$N$_3$O$_6$: C, 63.68; H, 7.05; N, 8.91. Found: C, 64.70; H, 7.12; N, 8.96.

EXAMPLE 54

5-(((2S)-2-(acetylamino-6-aminohexanoyl)amino)-N-(4-(aminosulfonyl)phenethyl)(1,1'-biphenyl)-2-carboxamide

EXAMPLE 54A

The product of example 46B was processed as in examples 4D, 1D, and 1B to provide the title compound.

MS (ESI–Q1MS) m/e 482 (M–H)$^+$, 965 (2M–H)$^+$.

EXAMPLE 54B

The product of example 54A and 4-(2-aminoethyl) benzenesulfonamide were processed as in examples 1E and 11 to provide the title compound.

MS (ESI+Q1MS) m/e 566 (M+H)$^+$; $^1$H NMR (300 MHz, DMSO-d6) δ 10.25 (br s, 1H), 8.35–8.05 (m, 2H), 7.91–7.60

(m, 4H), 7.45–7.22 (m, 6H), 4.40 (brm, 1H), 4.43–4.14 (brm, 3H), 2.84–2.66 (brm, 4H), 1.90 (brs, 3H), 1.80–1.28 (br, 6H).

EXAMPLE 55

Ethyl 2-(((5-(((2S)-2-(acetylamino)-6-aminohexanoyl)amino)(1,1'-biphenyl)-2-yl)carbonyl)amino)benzoate The product of example 43A and ethyl 2-aminobenzoate were processed as in examples 1E and 4D to provide the title compound.

MS (ESI+Q1MS) m/e 531 (M+H)$^+$;
$^1$H NMR (300 MHz, DMSO-d6) δ 10.76 (s, 1H), 10.53 (s, 1H), 8.36–8.24 (m, 1H), 8.02–7.57 (m, 6H), 7.45–7.15 (m, 5H), 4.44–4.36 (brm, 1H), 4.23 (q, 2H), 2.82–2.75 (brm, 2H), 1.91 (s, 3H), 1.81–1.55 (m, 4H), 1.48–1.32 (m, 2H), 1.27 (t, 3H).

EXAMPLE 56

Ethyl 3-(((5-(((2S)-2-(acetylamino)-6-aminohexanoyl)amino)(1,1'-biphenyl)-2-yl)carbonyl)amino)benzoate The product of example 43A and ethyl 3-aminobenzoate were processed as in examples 1E and 4D to provide the title compound.

MS (ESI+Q1MS) m/e 531 (M+H)$^+$; $^1$H NMR (300 MHz, DMSO-d6) δ 10.50 (s, 1H), 10.45 (s, 1H), 8.26 (d, 1H), 8.00 (br 2H), 7.87–7.75 (m, 3H), 7.66–7.56 (m, 2H), 7.39–7.28 (m, 4H), 4.41 (brm, 1H), 4.27 (q, 2H), 2.82–2.74 (brm, 2H), 1.90 (s, 3H), 1.82–1.57 (br m, 4H), 1.49–1.24 (br m, 5H includes 1.30, t, 3H).

EXAMPLE 57 ethyl 4-(((5-(((2S)-2-(acetylamino)-6-aminohexanoyl)amino)(1,1'-biphenyl)-2-yl)carbonyl)amino)benzoate The product of example 43A and ethyl 4-aminobenzoate were processed as in examples 1E and 4D to provide the title compound.

MS (ESI+Q1MS) m/e 531 (M+H)$^+$; $^1$H NMR (300 MHz, DMSO-d6) δ 10.47 (s, 1H), 10.32 (s, 1H), 8.27–8.18 (m, 1H), 8.00 (br 2H), 7.79–7.73 (m, 2H), 7.64–7.56 (m, 2H), 7.43–7.29 (m, 5H), 4.41 (brm, 1H), 4.30 (q, 2H), 2.82–2.73 (brm, 2H), 1.90 (s, 3H), 1.83–1.57 (br m, 4H), 1.49–1.24 (brm, 5H includes 1.32, t, 3H).

EXAMPLE 58

5-(((2S)-2-(acetylamino-6-aminohexanoyl)amino-N-(4-(aminosulfonyl)benzyl)(1,1'-biphenyl)-2-carboxamide The product of example 54A and 4-(aminomethyl) benzenesulfonamide were processed as in examples 1E and 11 to provide the title compound.

MS (ESI+Q1MS) m/e 552 (M+H)$^+$; $^1$H NMR (300 MHz, DMSO-d6) δ 10.26 (br s, 1H), 8.64–8.07 (m, 2H), 7.78–7.63 (m, 4H), 7.55–7.14 (m, 6H), 4.40 (brm, 1H), 4.43–4.14 (brm, 3H), 2.76 (brm, 2H), 1.89 (brs, 3H), 1.80–1.28 (br, 6H).

EXAMPLE 59

2-(((5-(((2S)-2-(acetylamino)-6-(((benzyloxy) carbonyl)amino)hexanoyl)amino)(1,1'-biphenyl)-2-yl)carbonyl)amino)benzoic acid The product of example 43A and ethyl 2-aminobenzoate were processed as in examples 1E and 1B to provide the title compound.

MS (ESI+Q1MS) m/e 635 (M+H)$^+$;
$^1$H NMR (300 MHz, DMSO-d6) δ 11.25 (s, 1H), 10.31 (s, 1H), 8.53–7.55 (m, 5H), 7.44–7.10 (m, 10H), 4.98 (s, 2H), 4.36 (m, 1H), 3.02–2.97 (q, 2H), 1.87 (s, 3H), 1.75–1.53 (br m, 4H), 1.46–1.24 (br m, 2H).

EXAMPLE 60

3-(((5-(((2S)-2-(acetylamino)-6-(((benzyloxy) carbonyl)amino)hexanoyl)amino)(1,1'-biphenyl)-2-yl)carbonyl)amino)benzoic Acid The product of example 43A and ethyl 3-aminobenzoate were processed as in examples 1E and 1B to provide the title compound.

MS (ESI+Q1MS) m/e 635 (M+H)$^+$;
$^1$H NMR (300 MHz, DMSO-d6) δ 10.25 (s, 2H), 8.19–7.56 (m, 5H), 7.42–7.22 (m, 10H), 5.00 (s, 2H), 4.38 (m, 1H), 3.02–2.97 (q, 2H), 1.88 (s, 3H), 1.76–1.57 (br m, 4H), 1.49–1.26 (br m, 2H).

EXAMPLE 61

4-(((5-(((2S1–2-(acetylamino)-6-(((benzyloxy) carbonyl)amino)hexanoyl)amino)(1,1'-biphenyl)-2-yl)carbonyl)aminobenzoic acid The product of example 43A and ethyl 4-aminobenzoate were processed as in examples 1E and 1B to provide the title compound.

MS (ESI+Q1MS) m/e 635 (M+H)$^+$; $^1$H NMR (300 MHz, DMSO-d6) δ 10.49 (d, 1H), 10.26 (s, 1H), 8.15–7.56 (m, 5H), 7.42–7.22 (m, 10H), 4.99 (s, 2H), 4.38 (brm, 1H), 3.02–2.97 (q, 2H), 1.88 (s, 3H), 1.76–1.56 (br m, 4H), 1.49–1.26 (br m, 2H).

EXAMPLE 62

2-(((5-(((2S)-2-(acetylamino)-6-aminohexanoyl) amino)(1,1'-biphenyl)-2-yl)carbonyl)amino)benzoic acid The product of example 59 was processed according to example 4D to yield the title compound, which was isolated as its acetate salt.

MS (ESI+Q1MS) m/e 503 (M+H)$^+$, 525 (M+Na)$^+$, 1005 (2M+H)$^+$; $^1$H NMR (300 MHz, DMSO-d6) δ 10.55 (br, 1H), 8.44–8.35 (br, 2H), 7.95 (br 1H), 7.76–7.52 (m, 3H), 7.40–7.18 (m, 6H), 4.40 (brm, 1H), 2.77 (brm, 2H), 1.90 (br s, 3H), 1.81–1.48 (br, 4H), 1.47–1.36 (br, 2H).

EXAMPLE 63

3-(((5-(((2S)-2-(acetylamino)-6-aminohexanoyl) amino)(1,1'-biphenyl-2-yl)carbonyl)amino)benzoic Acid The product of example 60 was processed according to example 4D to yield the title compound, which was isolated as its acetate salt.

MS (ESI+Q1MS) m/e 503 (M+H)$^+$, 1005 (2M+H)$^+$; $^1$H NMR (300 MHz, DMSO-d6) δ 10.63 (d, 1H), 10.07 (s, 1H), 8.53 (d, 1H), 8.04 (s, 1H), 7.78–7.73 (m, 2H), 7.62–7.52 (m, 3H), 7.43–7.18 (m, 6H), 4.38 (1brm, 1H), 2.77 (brm, 2H), 1.88 (s, 3H), 1.82–1.54 (br m, 4H), 1.51–1.31 (br m, 2H).

EXAMPLE 64

4-(((5-(((2S)-2-(acetylamino)-6-aminohexanoyl) amino)(1,1'-biphenyl-2-yl)carbonyl)amino)benzoic Acid The product of example 61 was processed according to example 4D to yield the title compound, which was isolated as its acetate salt.

MS (ESI+Q1MS) m/e 503 (M+H)+, 1005 (2M+H)+; $^1$H NMR (300 MHz, DMSO-d6) δ 10.70 (d, 1H), 10.22 (s, 1H), 8.52 (d, 1H), 7.82–7.74 (m, 4H), 7.56–7.49 (m, 3H), 7.41–7.27 (m, 5H), 4.40 (brm, 1H), 2.85–2.71 (brm, 2H), 1.88 (s, 3H), 1.81–1.55 (br m, 4H), 1.49–1.27 (br m, 2H).

What is claimed is:

1. A compound of Formula III

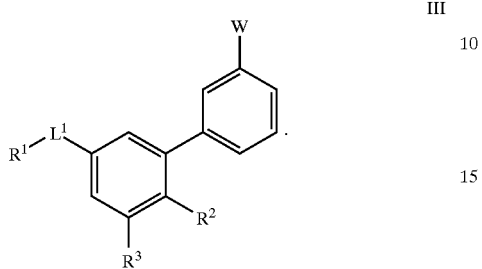

or a pharmaceutically acceptable salt or prodrug thereof, where $L^1$ is selected from
(1) —C(O)NR$^5$(CH$_2$)$_m$—, where m is an integer from 0 to 4, and
  $R^5$ is selected from
  (a) hydrogen
  and
  (b) alkyl,
and
(2) —N(R$^5$)C(O)(CH$_2$)$_m$—,
where (1) and (2) are drawn with their left ends attached to $R^1$;

$R^1$ is selected from
(1) alkyl,
(2) alkyl substituted with 1, 2, or 3 substituents selected from
  (a) —NO$_2$
  (b) —NR$^6$R$^7$ where R$^6$ and R$^7$ are independently selected from
    (i) hydrogen,
    (ii) alkyl,
    (iii) arylalkyl,
    (iv) an amino protecting group,
    (v) alkanoyl, where the alkanoyl can be optionally substituted with —OR$^9$,
    (vi) (aryl)oyl,
    (vii) alkoxycarbonyl,
    and
    (viii) (heteroaryl)oyl,
    and
  (c) alkoxycarbonyl,
(3) aryl substituted with 1, 2, 3, 4, or 5 substituents independently selected from
  (a) —NR$^6$R$^7$,
  (b) alkyl,
  and
  (c) alkyl substituted with 1, 2, or 3 substituents selected from —NR$^6$R$^7$,
(4) —NR$^6$R$^7$,
and
(5) —OR$^9$;

$R^2$ is selected from
(1) —(CH$_2$)$_n$C(O)R$^8$ where n is an integer from 0 to 4, and $R^8$ is selected from
(a) —OR$^9$ where R$^9$ is selected from
  (i) hydrogen,
  (ii) alkyl,
  and
  (iii) alkyl substituted with 1 or 2 substituents selected from the group consisting of aryl
and
(b) —NR$^5$R$^{10}$ where R$^5$ is defined previously, and R$^{10}$ is selected from
  (i) hydrogen,
  (ii) alkyl,
  (iii) alkyl substituted with 1, 2, or 3 substituents independently selected from
    (1') —CO$_2$R$^9$
    and
    (2') —C(O)NR$^6$R$^7$
  (iv) aryl, and
  (v) arylalkyl,
  where (iv) and (v) can be optionally substituted with 1, 2, 3, 4, or 5 substituents independently selected from
    (1') alkyl,
    (2') alkanoyl,
    (3') —OR$^9$,
    (4') —CO$_2$R$^9$,
    (5') alkanoyloxy,
    (6') carboxaldehyde,
    (7') cycloalkyl,
    (8') cycloalkenyl,
    (9') halo,
    (10') nitro,
    (11') perfluoroalkyl,
    (12') perfluoroalkoxy,
    (13') —NR$^6$R$^7$,
    (14') —SO$_2$NR$^6$R$^7$,
    (15') —C(O)NR$^6$R$^7$,
    (16') aryloxy,
    and
    (17') aryl,
    and
(2) aryl, wherein the aryl is optionally substituted with 1, 2, or 3 substituents independently selected from
  (a) —NR$^6$R$^7$
  and
  (b) —CO$_2$R$^9$;

$R^3$ is selected from
(1) hydrogen
(2) —(CH$_2$)$_n$C(O)R$^8$ where n is an integer from 0 to 4, and
  $R^8$ is selected from
  (a) —OR$^9$ where R$^9$ is selected from
    (i) hydrogen,
    (ii) alkyl,
    and
    (iii) alkyl substituted with 1 or 2 substituents selected from the group consisting of aryl
  and
  (b) —NR$^5$R$^{10}$ where R$^5$ is defined previously, and R$^{10}$ is selected from
    (i) hydrogen,
    (ii) alkyl,
    (iii) alkyl substituted with 1, 2, or 3 substituents independently selected from
      (1') —CO$_2$R$^9$
      and
      (2') —C(O)NR$^6$R$^7$ (iv) aryl, and
(v) arylalkyl
where (iv) and (v) can be optionally substituted with 1, 2, 3, 4, or 5 substituents independently selected from
(1') alkyl,
(2') alkanoyl,
(3') —OR$^9$,
(4') —CO$_2$R$^9$,
(5') alkanoyloxy,
(6') carboxaldehyde,
(7') cycloalkyl,
(8') cycloalkenyl,
(9') halo,
(10') nitro,
(11') perfluoroalkyl,
(12') perfluoroalkoxy,
(13') —NR$^6$R$^7$,
(14') —SO$_2$NR$^6$R$^7$,
(15') —C(O)NR$^6$R$^7$,
(16') aryloxy,
and
(17') aryl,
and
(3') aryl, wherein the aryl is optionally substituted with 1, 2, or 3 substituents independently selected from
(a') —NR$^6$R$^7$
and
(b') —CO$_2$R$^9$; and
W is selected from
(a) alkyl,
(b) alkanoyl,
(c) —OR$^9$,
(d) —CO$_2$R$^9$,
(e) alkanoyloxy,
(f) carboxaldehyde,
(g) cycloalkyl,
(h) cycloalkenyl,
(i) halo,
(j) nitro,
(k) perfluoroalkyl,
(l) perfluoroalkoxy,
(m) —NR$^6$R$^7$,
(n) —SO$_2$NR$^6$R$^7$,
(o) —C(O)NR$^6$R$^7$,
(p) aryloxy,
and
(q) aryl.

2. A compound according to claim 1 selected from the group consisting of
(S)-methyl 4-[[2-[[(1,1dimethylethoxy)carbonyl]amino]-6-[(phenylmethoxy)carbonyl]amino]1-oxohexyl]amino]-2-[3-(phenylmethoxy)phenyl]benzoate,
(S)-1,1-dimethylethyl 4-[[2-[[(1,1-dimethylethoxy)carbonyl]amino]-6-[(phenylmethoxy)carbonyl]amino]-1-oxohexyl]amino]-2-[3-(phenylmethoxy)phenyl]benzoate,
(R)-methyl 4-[[6-amino-2-[[(1,1-dimethylethoxy)carbonyl]amino]-1-oxohexyl]amino]-2-(3-hydroxyphenyl)benzoate,
(S)-methyl 4-[[2-amino-6-[[(phenylmethoxy)carbonyl]amino-1-oxohexyl]amino]-2-[(3-phenylmethoxy)phenyl]benzoate,
(S)-methyl 4-[[2-(acetylamino)-6-[[(phenylmethoxy)carbonyl]amino]-1-oxohexyl]amino]-2-[(3-(phenylmethoxy)phenyl]benzoate,
(S)-1,1-dimethylethyl 4-[[6-amino-2-[[(1,1-dimethylethoxy)carbonyl]amino]-1-oxohexyl]amino]-2-(3-hydroxyphenyl)benzoate,
(S)-methyl 4-[[2-(acetylamino)-6-amino-1-oxohexyl]amino]-2-(3-hydroxyphenyl)benzoate,
(S)-4-[[2-(acetylamino)-6-amino-1-oxohexyl)amino]-2-(3-hydroxyphenyl)benzoic acid,
(S)-N-[4-[[2-(acetylamino)-6-amino-1-oxohexyl]amino]-2-(3-hydroxyphenyl)benzoyl]-L-α-asparagine,
tert-butyl (3S)-3-(((5-(((2S)-2-(acetylamino)-6-aminohexanoyl)amino)-3'-hydroxy(1,1'-biphenyl)-2-yl)carbonyl)amino)-4-amino-4-oxobutanoate,
5-(((2S)-6-amino-2-(tert-butoxycarbonyl)amino) hexanoyl)amino)-3'hydroxy(1,1'-biphenyl)-2-carboxylic acid,
methyl 5-(((2S)-2,6-diaminohexanoyl)amino)-3'-hydroxy (1,1'-biphenyl)-2-carboxylate,
5-(((2S)-6-amino-2-((2,2-dimethylpropanoyl)amino) hexanoyl)amino)-3'-hydroxy(1,1'-biphenyl)-2-carboxylic acid,
methyl-5-(((2S)-6-amino-2-((2,2-dimethylpropanoyl) amino)hexanoyl)amino)-3'-hydroxy(1,1'-biphenyl)-2-carboxylate,
5-(((2S)-6-amino-2-(benzoylamino)hexanoyl)amino)-3'hydroxy(1,1'-biphenyl)-2-carboxylic acid,
5-(((2S)-6-amino-2-((methoxycarbonyl)amino)hexanoyl) amino)-3'-hydroxy(1,1'-biphenyl)-2-carboxylic acid,
methyl 5-(((2S)-2-((tert-butoxycarbonyl)amino) hexanoyl)amino)-3'-hydroxy(1,1'-biphenyl)-2-carboxylic,
5-(((2S)-2-(tert-butoxycarbonyl)amino)-6-((3-pyridinylcarbonyl)amino)hexanoyl)amino)-3'-hydroxy (1,1'-biphenyl)-2-carboxylic acid,
5-((6-aminohexanoyl)amino)-3'-hydroxy(1,1'-biphenyl)-2-carboxylic acid,
5(((2S)-2-((tert-butoxycarbonyl)amino)hexanoyl)amino)-3'-hydroxy(1,1'-biphenyl)2-carboxylic acid,
5-(((2S)-5-amino-2-((tert-butoxycarbonyl)amino) pentanoyl)amino)-3'-hydroxy(1,1,'-biphenyl)-2-carboxylic acid, and
5-(((2S)-2-((tert-butoxycarbonyl)amino)-6-(methylamino)hexanoyl)amino)-3'-hydroxy(1,1'-biphenyl)-2-carboxylic acid.

3. A compound of Formula IV

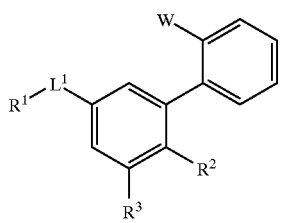

or a pharmaceutically acceptable salt or prodrug thereof, where
L$^1$ is selected from
(1) —C(O)NR$^5$(CH$_2$)$_m$—, where m is an integer from 0 to 4, and
R$^5$ is selected from
(a) hydrogen
and (b) alkyl,
and
(2) —N(R$^5$)C(O)(CH$_2$)$_m$—,
where (2) and (3) are drawn with their left ends attached to R$^1$;
R$^1$ is selected from
(1) alkyl,
(2) alkyl substituted with 1, 2, or 3 substituents selected from
   (a) —NO$_2$,
   (b) —NR$^6$R$^7$ where R$^6$ and R$^7$ are independently selected from
     (i) hydrogen,
     (ii) alkyl,
     (iii) arylalkyl,
     (iv) an amino protecting group,
     (v) alkanoyl, where the alkanoyl can be optionally substituted with —OR$^9$,
     (vi) (aryl)oyl,
     (vii) alkoxycarbonyl,
     and
     (viii) (heteroaryl)oyl,
   and
   (c) alkoxycarbonyl,
(3) aryl substituted with 1, 2, 3, 4, or 5 substituents independently selected from
   (a) —NR$^6$R$^7$,
   (b) alkyl,
   and
   (c) alkyl substituted with 1, 2, or 3 substituents selected from —NR$^6$R$^7$,
(4) —NR$^6$R$^7$,
and
(5) —OR$^9$;
R$^2$ is selected from
(1) —(CH$_2$)$_n$C(O)R$^8$ where n is an integer from 0 to 4,
and
R$^8$ is selected from
   (a) —OR$^9$ where R$^9$ is selected from
     (i) hydrogen,
     (ii) alkyl,
     and
     (iii) alkyl substituted with 1 or 2 substituents selected from the group consisting of aryl
   and
   (b) —NR$^5$R$^{10}$ where R$^5$ is defined previously, and R$^{10}$ is selected from
     (i) hydrogen,
     (ii) alkyl,
     (iii) alkyl substituted with 1, 2, or 3 substituents independently selected from
       (1') —CO$_2$R$^9$
       and
       (2') —C(O)NR$^6$R$^7$
     (iv) aryl, and
     (v) arylalkyl,
     where (iv) and (v) can be optionally substituted with 1, 2, 3, 4 or 5 substituents independently selected from
       (1') alkyl,
       (2') alkanoyl,
       (3') —OR$^9$,
       (4') —CO$_2$R$^9$,
       (5') alkanoyloxy,
       (6') carboxaldehyde,
       (7') cycloalkyl,
       (8') cycloalkenyl,
       (9') halo,
       (10') nitro,
       (11') perfluoroalkyl,
       (12') perfluoroalkoxy,
       (13') —NR$^6$R$^7$,
       (14') —SO$_2$NR$^6$R$^7$,
       (15') —C(O)NR$^6$R$^7$,
       (16') aryloxy,
       and
       (17') aryl,
     and
(2) aryl, wherein the aryl is optionally substituted with 1, 2, or 3 substituents independently selected from
   (a) —NR$^6$R$^7$
   and
   (b) —CO$_2$R$^9$;
R$^3$ is selected from
(1) hydrogen
(2) —(CH$_2$)$_n$C(O)R$^8$ where n is an integer from 0 to 4, and
R$^8$ is selected from
   (a) —OR$^9$ where R$^9$ is selected from
     (i) hydrogen,
     (ii) alkyl,
     and
     (iii) alkyl substituted with 1 or 2 substituents selected from the group consisting of aryl
   and
   (b) —NR$^5$R$^{10}$ where R$^5$ is defined previously, and R$^{10}$ is selected from
     (i) hydrogen,
     (ii) alkyl,
     (iii) alkyl substituted with 1, 2, or 3 substituents independently selected from
       (1') —CO$_2$R$^9$
       and
       (2') —C(O)NR$^6$R$^7$
     (iv) aryl, and
     (v) arylalkyl,
     where (iv) and (v) can be optionally substituted with 1, 2, 3, 4 or 5 substituents independently selected from
       (1') alkyl,
       (2') alkanoyl,
       (3') —OR$^9$,
       (4') —CO$_2$R$^9$,
       (5') alkanoyloxy,
       (6') carboxaldehyde,
       (7') cycloalkyl,
       (8') cycloalkenyl,
       (9') halo,
       (10') nitro,
       (11') perfluoroalkyl,
       (12') perfluoroalkoxy,
       (13') —NR$^6$R$^7$,
       (14') —SO$_2$NR$^6$R$^7$,
       (15') —C(O)NR$^6$R$^7$,
       (16') aryloxy,
       and
       (17') aryl, and
(3') aryl, wherein the aryl is optionally substituted with 1, 2, or 3 substituents independently selected from
   (a) —NR$^6$R$^7$
   and
   (b) —CO$_2$R$^9$;

and W is selected from
(a) alkyl,
(b) alkanoyl,
(c) —$OR^9$,
(d) —$CO_2R^9$,
(e) alkanoyloxy,
(f) carboxaldehyde,
(g) cycloalkyl,
(h) cycloalkenyl,
(i) halo,
(j) nitro,
(k) perfluoroalkyl,
(l) perfluoroalkoxy,
(m) —$NR^6R^7$,
(n) —$SO_2NR^6R^7$,
(o) —$C(O)NR^6R^7$,
(p) aryloxy,
and
(q) aryl.

4. A compound according to claim 3, selected from
(R)-methyl 4-[[6-amino-2-[[(1,1-dimethylethoxy)carbonyl]amino]-1-oxohexyl]amino]-2-(2-hydroxyphenyl)benzoate,
methyl 5-(((2S)-6-amino-2-((tert-butoxycarbonyl)amino)hexanoyl)amino)-4'-hydroxy(1,1'-biphenyl)-2-carboxylate, and
(3S)-3-(((5-(((2S)-2-(acetylamino)-6-aminohexanoyl)amino)-4'-hydroxy(1,1'-biphenyl)-2-yl)carbonyl)amino)-4-amino-4-oxobutanoic acid.

* * * * *

UNITED STATES PATENT AND TRADEMARK OFFICE
CERTIFICATE OF CORRECTION

PATENT NO.   : 6,849,757 B2
DATED        : July 10, 2003
INVENTOR(S)  : Megumi Kawai et al.

It is certified that error appears in the above-identified patent and that said Letters Patent is hereby corrected as shown below:

<u>Column 38,</u>
Line 32, replace "carboxylic" with -- carboxylate --.

Signed and Sealed this

Seventh Day of March, 2006

JON W. DUDAS
*Director of the United States Patent and Trademark Office*

UNITED STATES PATENT AND TRADEMARK OFFICE
CERTIFICATE OF CORRECTION

PATENT NO. : 6,849,757 B2
DATED : February 1, 2005
INVENTOR(S) : Megumi Kawai et al.

It is certified that error appears in the above-identified patent and that said Letters Patent is hereby corrected as shown below:

Column 38,
Line 32, replace "carboxylic" with -- carboxylate --.

This certificate supersedes Certificate of Correction issued March 7, 2006.

Signed and Sealed this

Eleventh Day of April, 2006

JON W. DUDAS
*Director of the United States Patent and Trademark Office*